(12) United States Patent
Averbuch

(10) Patent No.: US 9,743,896 B2
(45) Date of Patent: Aug. 29, 2017

(54) SURGICAL DEVICES AND METHODS OF USE THEREOF

(71) Applicant: Body Vision Medical Ltd., Ramat Hasharon (IL)

(72) Inventor: Dorian Averbuch, Ramat Hasharon (IL)

(73) Assignee: Body Vision Medical, Ramat Hasharon, IL (US)

( * ) Notice: Subject to any disclaimer, the term of this patent is extended or adjusted under 35 U.S.C. 154(b) by 0 days.

(21) Appl. No.: 14/433,414

(22) PCT Filed: Jan. 6, 2015

(86) PCT No.: PCT/IB2015/000438
§ 371 (c)(1),
(2) Date: Apr. 3, 2015

(87) PCT Pub. No.: WO2015/101948
PCT Pub. Date: Jul. 9, 2015

(65) Prior Publication Data
US 2016/0302747 A1 Oct. 20, 2016

Related U.S. Application Data

(60) Provisional application No. 61/923,956, filed on Jan. 6, 2014, provisional application No. 62/013,726, filed (Continued)

(51) Int. Cl.
*A61B 6/00* (2006.01)
*A61B 6/12* (2006.01)
(Continued)

(52) U.S. Cl.
CPC ............... *A61B 6/487* (2013.01); *A61B 6/12* (2013.01); *A61B 6/4441* (2013.01);
(Continued)

(58) Field of Classification Search
CPC ........... A61B 6/487; A61B 34/20; A61B 6/12; A61B 6/4441; A61B 6/5205;
(Continued)

(56) References Cited

U.S. PATENT DOCUMENTS

| 8,831,706 B2* | 9/2014 | Fu .......................... A61B 6/032 378/65 |
| 2001/0007919 A1* | 7/2001 | Shahidi .................... A61B 5/06 600/427 |

(Continued)

*Primary Examiner* — Sean Conner
*Assistant Examiner* — Pinalben Patel
(74) *Attorney, Agent, or Firm* — Greenberg Traurig LLP

(57) ABSTRACT

The present invention provides a method, including: obtaining a first image from a first imaging modality; identifying on the first image from the first imaging modality obtaining a second image from a second imaging modality; generating a compatible virtual image from the first image from the first imaging modality; mapping planning data on the compatible virtual image; coarse registering of the second image from the second imaging modality to the first image from the first imaging modality; identifying at least one element of the mapped planning data from the compatible virtual image; identifying at least one corresponding element on the second imaging modality; mapping the at least one corresponding element on the second imaging modality; fine registering of the second image from the second imaging modality to the first image from the first imaging modality; generating a third image.

11 Claims, 15 Drawing Sheets

Related U.S. Application Data on Jun. 18, 2014, provisional application No. 62/052,039, filed on Sep. 18, 2014.

(51) Int. Cl.

| | |
|---|---|
| *G06T 7/20* | (2017.01) |
| *G06T 19/00* | (2011.01) |
| *G06T 5/00* | (2006.01) |
| *A61B 34/20* | (2016.01) |
| *G06T 7/00* | (2017.01) |
| *G06T 7/33* | (2017.01) |
| *A61B 90/00* | (2016.01) |
| *A61B 6/03* | (2006.01) |

(52) U.S. Cl.
CPC .......... *A61B 6/5205* (2013.01); *A61B 6/5235* (2013.01); *A61B 34/20* (2016.02); *G06T 5/002* (2013.01); *G06T 7/0012* (2013.01); *G06T 7/20* (2013.01); *G06T 7/33* (2017.01); *G06T 19/006* (2013.01); *A61B 6/032* (2013.01); *A61B 6/5223* (2013.01); *A61B 2034/2048* (2016.02); *A61B 2034/2051* (2016.02); *A61B 2090/367* (2016.02); *A61B 2090/376* (2016.02); *G06T 2207/10081* (2013.01); *G06T 2207/10088* (2013.01); *G06T 2207/10116* (2013.01); *G06T 2207/10121* (2013.01); *G06T 2207/20016* (2013.01); *G06T 2207/30061* (2013.01); *G06T 2207/30096* (2013.01); *G06T 2207/30101* (2013.01)

(58) Field of Classification Search
CPC .......... A61B 6/5235; A61B 2034/2051; G06T 5/002; G06T 7/0012; G06T 7/0028; G06T 7/20; G06T 19/006; G06T 2207/10081; G06T 2207/10088; G06T 2207/10121; G06T 2207/20016; G06T 2207/30061; G06T 2207/30096; G06T 2207/30101
See application file for complete search history.

(56) References Cited

U.S. PATENT DOCUMENTS

| | | | |
|---|---|---|---|
| 2008/0262342 A1* | 10/2008 | Averbruch | A61B 6/12 600/424 |
| 2009/0234175 A1 | 9/2009 | Maier | |
| 2009/0281566 A1* | 11/2009 | Edwards | A61B 6/541 606/214 |
| 2010/0061611 A1* | 3/2010 | Xu | G06T 7/003 382/131 |
| 2010/0210939 A1* | 8/2010 | Hartmann | A61B 19/5244 600/424 |
| 2010/0316278 A1* | 12/2010 | Hartung | A61B 6/466 382/131 |
| 2013/0023766 A1* | 1/2013 | Han | A61B 6/5247 600/427 |
| 2013/0235198 A1* | 9/2013 | Chhabra | G06T 7/2053 348/143 |
| 2013/0293578 A1* | 11/2013 | Leung | G06F 3/147 345/633 |
| 2013/0303893 A1* | 11/2013 | Duindam | A61B 5/066 600/424 |
| 2014/0142422 A1 | 5/2014 | Manzke | |

* cited by examiner

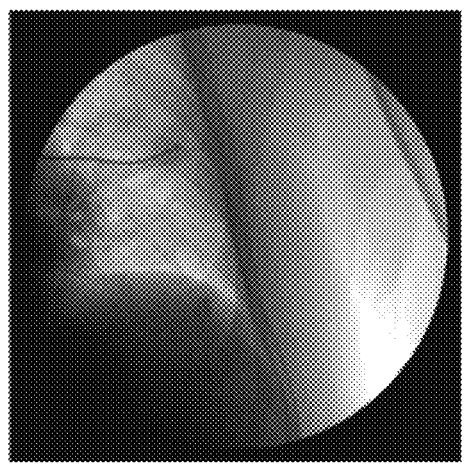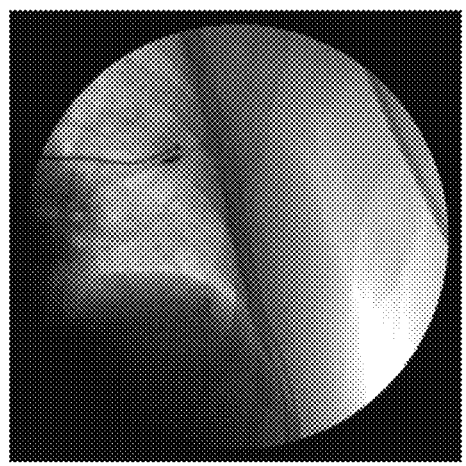
Original Image
FIGURE 3A
Augmented Image
FIGURE 3B

SURGICAL DEVICES AND METHODS OF USE THEREOF

RELATED APPLICATIONS

This application claims the priority of U.S. provisional application Ser. No. 61/923,956, entitled "AUGMENTED FLUOROSCOPY," filed Jan. 6, 2014, U.S. provisional application Ser. No. 62/013,726, entitled "AUGMENTED FLUOROSCOPY," filed Jun. 18, 2014, and U.S. provisional application Ser. No. 62/052,039, entitled "AUGMENTED FLUOROSCOPY," filed Sep. 18, 2014, which are incorporated herein by reference in their entireties for all purposes.

FIELD OF THE INVENTION

The embodiments of the present invention relate to surgical devices and methods of use thereof.

BACKGROUND OF INVENTION

Use of video-assisted thoracic surgery (VATS) during endoscopic surgery, as well as other fields of surgery, can be used during the treatment of various respiratory diseases.

BRIEF SUMMARY OF INVENTION

In some embodiments, the instant invention provides a method, including: obtaining a first image from a first imaging modality; identifying on the first image from the first imaging modality at least one element, where the at least one element comprises a landmark, an area of interest, an incision point, a bifurcation, an organ, or any combination thereof, obtaining a second image from a second imaging modality; generating a compatible virtual image from the first image from the first imaging modality; mapping planning data on the compatible virtual image; where mapped planning data corresponds to the at least one element, coarse registering of the second image from the second imaging modality to the first image from the first imaging modality; identifying at least one element of the mapped planning data from the compatible virtual image; identifying at least one corresponding element on the second imaging modality; mapping the at least one corresponding element on the second imaging modality; fine registering of the second image from the second imaging modality to the first image from the first imaging modality; generating a third image; where the third image is an augmented image including a highlighted area of interest.

In some embodiments, the method further includes superimposing the at least one image, a portion of the at least one image, or a planning information derived from the first imaging modality over the second imaging modality. In some embodiments, the method further includes using at least one instruction, where the at least one instruction can include information regarding navigation, guidance, or a combination thereof. In some embodiments, the guidance includes information regarding a positioning of a device shown the second imaging modality, where the device comprises a fluoroscopic C-Arm, as to result in achieving visibility for the area of interest, incision points, anatomical structures, or tool access direction. In some embodiments, the method further includes tracking of at least one anatomical structure by use of at least one subsequent image derived from the second imaging modality, where the second imaging modality comprises a fluoroscopic video configured to have substantially the same acquisition parameters, and where the acquisition parameters comprise mode, position, field of view, or any combination thereof, to generate the augmented fluoroscopic image by suppressing static anatomic structures and/or improving signal to noise of underlying soft tissue. In some embodiments, the method further includes performing a multiphase registration, where the at least one substantially static object is first registered; and where at least one dynamic object is second registered, where the at least one dynamic object comprises a diaphragm, a bronchus, a blood vessel, or any combination thereof. In some embodiments, the method further includes deemphasizing at least one interfering structure. In some embodiments, the compatible virtual image is not generated while the planning data from first imaging modality is transferred to second imaging modality by means of image registration.

In some embodiments, the instant invention provides a method, including:
using at least two intraoperative images with known relative movement and rotation to generate a grouping of pixels derived from an intraoperative image, where the grouping of pixels is determined by individual calculation of each pixel using: (a) movement variation of each pixel and (b) intensity values of each pixel; performing registration using at least two sequential intraoperative images to reconstruct structures in an area of interest; differentiating moving structures from static structures in the area of interest; and highlighting anatomical structures on at least one intraoperative image. In some embodiments, the method further includes using a chest x-ray radiographic image as a first intraoperative image.

In some embodiments, the instant invention provides a system including an augmented fluoroscopy device configured to generate an augmented fluoroscopy image including (a) video and image processing unit, (b) video input card or externally connected device configured to input video signal a fluoroscopic device, (c) 3D planning input in internal or DICOM format, (d) an augmented video signal output, or any combination thereof. In some embodiments, the system is integrated with at least one fluoroscopic device is a module including a RAW data input card (i.e., instead of a video input card) configured to obtain RAW data as a signal. In some embodiments, the system is integrated with a Cone-beam CT system.

In some embodiments, the instant invention provides a system including an instrument for navigating inside natural body cavity including: (a) a guided sheath with anchoring at the tip and/or (b) a guided wire. In some embodiments, the instrument is an inflatable balloon configured to act as an anchoring mechanism.

In some embodiments, the instant invention provides a method including: (i) selecting a volume of interest on a first image from a first imaging modality; (ii) generating a second image from a second imaging modality; (iii) coarse registering using the first imaging modality and the second imaging modality; (iv) producing at least one pattern from the first imaging modality; (v) generating a matching pattern by use of the second imaging modality using single or multiple patterns produced from first imaging modality; (vi) enhancing the matching pattern from the second imaging modality to highlight the anatomy in the volume of interest for producing third imaging modality. In some embodiments, the anatomic structures located outside the area of interest are found and suppressed using substantially the same method. In some embodiments, the pattern includes anatomical features including, but not limited to, airways, ribs, and blood vessels. In some embodiments, the matching feature from second imaging modality is derived from a set of at least one instrument position inside the area of interest.

In some embodiments, the instant invention provides a method including: using a first imaging modality to obtain at least one first image of a patient's chest; segmenting natural body cavities including bronchial airways in a 3D space; generating at least one image from a second imaging modality; generating a two-dimensional augmented image generated from the second imaging modality by combining information, where the information describes a complete map or a partial map of natural body cavities, including a bronchial airway tree; calculating registration between the first imaging modality and the second imaging modality as pose estimation between the portion of bronchial airway sourcing from second imaging modality and segmented map of bronchial airway sourcing from first imaging modality; calculating registration between first and second imaging modalities through pose estimation by mapping corresponding features. In some embodiments, the augmented bronchogram is generated using radiopaque material is injected to highlight the body cavity. In some embodiments, the augmented bronchogram is generated through superposition of imaging from at least three two different positions of radiopaque instrument located inside the body cavities. In some embodiments, an augmented bronchogram is generated through superposition of imaging from at least one different positions of radiopaque instrument located inside the body cavity and angular measurement of C-Arm orientation relative to patient bed. In some embodiments, the radiopaque instrument is designed and configured to reconstruct its three-dimensional space from single projection. In some embodiments, the radiopaque substance(s) having a high viscosity such as, but not limited to, hydrogel, reverse thermo-gelling polymer can be used to generate augmented bronchogram.

In some embodiments, the instant invention provides a method including: providing the parameters of compatable virtual image sourcing from first imaging modality, such as, but not limited to, DDR—to fluoroscopy; determining an object size on virtual image, such as, but not limited to, ribs width on DDR at specific location; providing the pose and field of view of a virtual camera, such as, but not limited to, a virtual fluoroscopic camera, projecting first imaging modality to second imaging modality such as fluoroscopic camera calculated from calibration process; determining the object size on the virtual image, such as ribs width on DDR at specific location; calculating the depth (for example, but not limited to, distance of the specific object or object area from fluoroscopic X-ray source) through comparison between the known object sizes sourced from first image (e.g. CT image) to the one measured on second image (e.g. fluoroscopic image). In some embodiments, the object size is determined from technical specification instead of or in addition to the measurement on compatible virtual image, such as tool rigid part length or width. In some embodiments, the catheter-type tool is designed to allow the calculation of trajectory as a combination of depth distances from second imaging modality camera center.

BRIEF DESCRIPTION OF THE DRAWINGS

The present invention will be further explained with reference to the attached figures. The figures constitute a part of this specification and include illustrative embodiments of the present invention and illustrate various objects and features thereof. Specific functional details disclosed herein are not to be interpreted as limiting, but merely as a representative basis for teaching one skilled in the art to variously employ the present invention.

FIGS. 3A and 3B are images illustrating an embodiment of the method of the present invention.

FIG. 15A is a first image (e.g., an original image)

and FIG. 15B is a second image having a highlighted section (e.g., shown in a dashed circle).

DESCRIPTION

Figure 1:
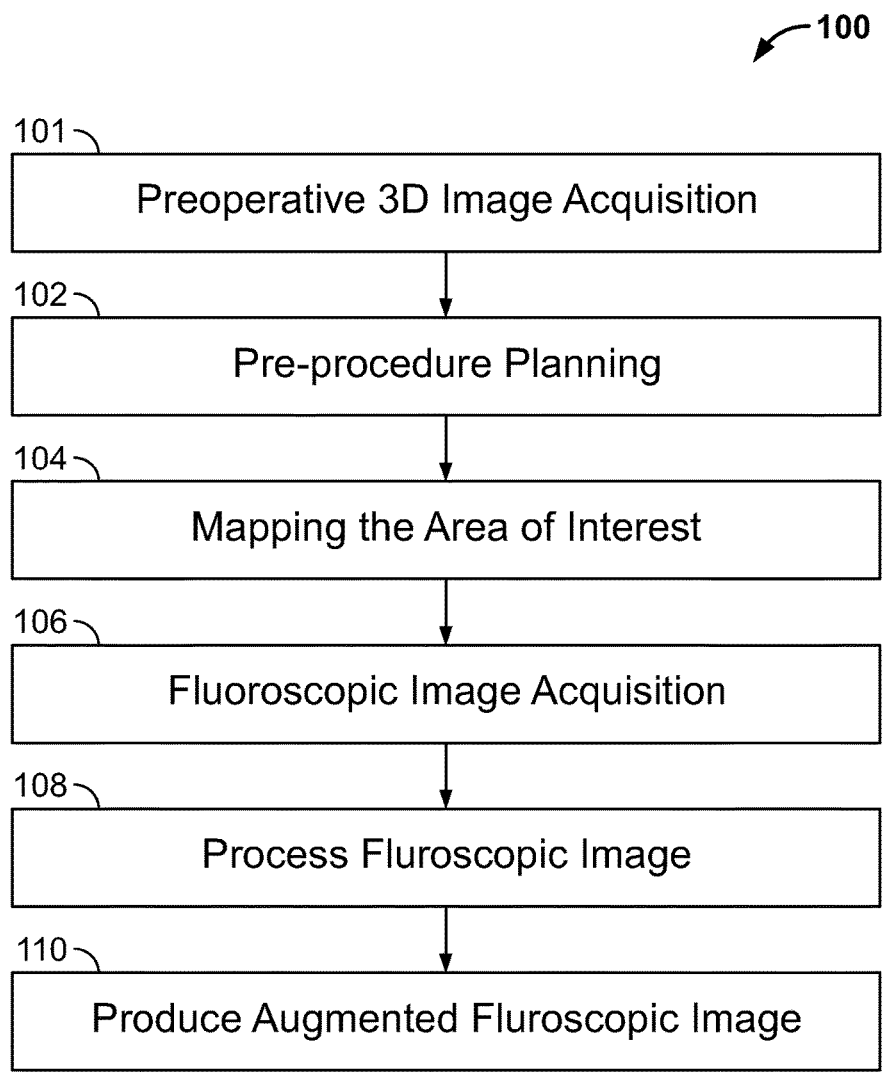
FIG. 1 is a flow chart illustrating an embodiment of the present invention, showing a surgical and diagnostic procedure flow chart.

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the Figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, "coarse registration" refers to a rough alignment of a preoperative and an intraoperative image. In some embodiments of the method of the present invention, coarse registration uses global information and does not take into account local tissue deformation caused by breathing, instrument movement, pose difference between preoperative and intraoperative images, etc.

As used herein, an "element" refers to a unit of anatomy that has a common mechanical characteristic, for example, a mechanical property (e.g., but not limited to, a rigidity of movement, flexibility, strength). In some embodiments, elements can be, but are not limited to, bronchi, vessels, ribs, image patterns, etc.

As used herein, "fine registration" refers to the registration of local tissue (e.g., but not limited to, soft tissue) around an area of interest of a first image (e.g., a preoperative image), which corresponds to an area of a second image (e.g., an intraoperative image). In some embodiments of the method of the present invention, fine registration is a technique/method designed to correct local tissue deformation and/or relative tissue movement (e.g., but not limited to, movement divergence between ribs and lungs during breathing) inside an area of interest, e.g., but not limited to, a local proximity of a tool tip, a pre-marked nodule area, etc. In some embodiments, fine registration further allows for improvement of local registration accuracy over coarse registration in an area of interest, while coarse registration output, such as transformation matrix, projected primitives, output images, etc., are supplied as input for use of the fine registration.

As used herein, "mapping" refers to transferring a plurality of elements from a first image of a first imaging modality to a second image of a second imaging modality. In some embodiments, mapping can include: (1) identifying a plurality of elements of a first image (2) identifying a plurality of elements of a second image, (3) pairing the plurality of elements of the first/second image to a corresponding plurality of elements of a second/first image, (4) registering (i.e., registration) a plurality of elements of the first/second image to corresponding pairs of the plurality of elements of a second/first image. In some embodiments, the registering is performed by fine and/or coarse registration. As a non-limiting example, mapping can include (1) identifying a plurality (e.g., but not limited to, 2, 3, 4, 5, 6, 7, 8, 9, 10, etc., elements) of elements (e.g., bronchi, ribs, etc.) from a first image (e.g., a CT image), (2) identifying a plurality of fluoroscopic elements on the first image (e.g., a CT image) and a plurality of fluoroscopic elements on the second image (e.g., a fluoroscopic image) (3) pairing a subset of the plurality of elements that are corresponding elements (i.e., to bronchi, ribs) on a second image, (4) registering the elements to the corresponding pairs of the elements on the second image, where the mapping results in a representation of the airway of the first image, or any combination thereof. In some embodiments, an image can be derived from a raw image, e.g., but not limited to, a DDR image, an edited image, a processed image, etc.

In some embodiments, although the term "preoperative image" is used to describe the invention it will be apparent to one skilled in the art that the same concept can be applied when the reference image such as CT, MRI or X-Ray Radiograph imaging is acquired intraoperatively. In some embodiments, the method of the present invention is applicable for the imaging performed with or without contrast medium.

In some embodiments, the present invention is a method that allows using a first imaging modality (such as CT, MRI, etc.) and planning information by generating an augmented image using a second imaging modality, such as, but not limited to, fluoroscopy, digital subtraction angiography (DSA), etc. In some embodiments, the method further includes highlighting an area of interest and/or structures. In some embodiments, the method can include additional imaging and/or planning information, where the additional imaging and/or planning information can be originated/generated from a first imaging modality, and can include superimposing, as non-limiting examples: (i) a first imaging modality for use in obtaining at least one first image of chest; (ii) manual and/or automatic planning of a surgical procedure through defining landmarks, area of interest, incision points, critical structures, bifurcations, anatomical organs, etc.; (iii) at least one second image obtained from second imaging modality, such as, but not limited to, fluoroscopy and/or DSA, and generation of compatible virtual image, such as a digitally reconstructed radiograph (DRR), from a first imaging modality; (iv) a map ("mapping") of planning data to at least one object and/or structure on the compatible virtual image; (v) a registration of at least one second image or video frame from second imaging modality to first image or its portion sourced from first imaging modality; (vi) planning data identified from the compatible virtual image, sourced from first imaging modality to at least one second image from second imaging modality by means of image registration; (vii) planning data mapped from the compatible virtual image, sourced from first imaging modality to at least one second image from second imaging modality by means of image registration; (viii) a highlighted area of interest, e.g., but not limited to, at least one anatomical structure on the at least one second image sourced from second imaging modality to obtain at least one third image, wherein the at least one third image is augmented, or any combination thereof.

In some embodiments, the method further includes superimposing of at least one image or a derivative of the at least one image, a portion of the at least one image or image based planning information sourced from the first imaging modality. In other embodiments, the method further includes navigation and guidance instructions that aid movement of medical instrument. In some embodiments, the method further includes guidance for positioning the second imaging modality, such as use of a fluoroscopic C-Arm, to allow maintaining optimal visibility for an area of interest. In some embodiments, the method further includes tracking of an anatomic structure(s) on subsequent frames from second imaging modality, such as, but not limited to, fluoroscopic video, having substantially the same acquisition parameters, where the acquisition parameters can include, but are not limited to, mode, position, field of view, to result in generating a augmented fluoroscopic image, where the augmented fluoroscopic image is generated by suppression of a static anatomic structure(s) and/or improving signal to noise ratio of underlying soft tissue. In some embodiments, the method includes performing multiphase registration, where at least one static object(s) having small movement(s) (e.g., but not limited to, 2-5 centimeters), such as, e.g. but not limited to ribs, are first registered. In some embodiments, after the static object(s) are first registered, more dynamic objects such as, but not limited to, diaphragm, bronchi, blood vessels, etc. are registered in the following registration iterations. In some embodiments, the method further includes the interfering structures (e.g., any structure that could interfere with an anatomical focus of a procedure (e.g., but not limited to removing ribs from an image focusing on vessels)) being deemphasized.

In some embodiments, the method of the present invention allows for the generation of at least one augmented third image, such as, but not limited to, an intraoperative fluoroscopic image, a DSA image, etc., having a highlighted area of interest and/or structures that can include, but is not limited to: (i) using at least two intraoperative images with known relative movement and/or rotation to allow for the grouping of pixels of the at least two intraoperative images according to the movement variation and/or intensity values of the at least two intraoperative images; (ii) performing registration and/or cross-correlation between at least two sequential intraoperative images to reconstruct structures in the area of interest; (iii) differentiating moving and static structures in the area of interest based on user demand; (iv) highlighting anatomical structures an intraoperative image, or any combination thereof.

In some embodiments, the method of the present invention further includes using an x-ray radiographic image of a patient's chest, while the x-ray radiographic image can serve as a reference image for enabling an enhancement of at least one anatomical structure on a second image by use of an analogous process, i.e., cross-correlation of the information from radiographic image obtained with different energy levels.

In some embodiments, the present invention is an augmented fluoroscopy device that allows for the generation of at least one augmented fluoroscopy image, where the augmented fluoroscopy device can include, but is not limited to: (i) a video and image processing unit; (ii) a video input card and/or externally connected device configured to input video signal from a fluoroscopic device; (iii) 3D planning input in internal and/or DICOM format; (iv) augmented video signal output, or any combination thereof.

In some embodiments, the device of the present invention is integrated within a fluoroscopic device (i.e., as a module) to obtain RAW data as a signal, and includes a RAW data input card. In some embodiments, the device has a RAW data card instead of a video input card. In some embodiments, the present invention is integrated within a Cone-beam CT system.

In some embodiments, the present invention is a method for highlighting a tissue or an anatomical structure, where the method can include: (i) selecting the volume of interest on the image sourcing from first imaging modality, such as, but not limited to, CT and/or MRI; (ii) acquiring an image from a second imaging modality; (iii) performing coarse registration between a second imaging modality and a first imaging modality to identify the pose of a virtual camera in the second imaging modality correspondent to the one of second imaging modality; (iv) producing at least one pattern from first the imaging modality for the anatomical structure around a volume of interest is produced; (v) identifying a matching pattern in the second imaging modality using a single pattern or multiple patterns produced from the first imaging modality; (vi) highlighting (i.e., enhancing) a matching pattern from the second imaging modality to enhance the anatomy in the volume of interest on third imaging modality, or any combination thereof.

In some embodiments, the method includes finding and suppressing anatomic structures located outside the area of interest.

In some embodiments, the present invention includes a method of object depth calculation that includes, but is not limited to: (i) providing parameters of compatible virtual image sourcing from the first imaging modality, (as a non-limiting example, the first imaging modality can be, but is not limited to, DDR—to fluoroscopy); (ii) determining the object size on a virtual image, such as ribs width on DDR at a specific location; (iii) providing the pose and field of view of the second image (as a non-limiting example: a fluoroscopic camera calculated from a calibration process); (iv) calculating the depth (such as, but not limited to, a distance of a specific object or an object area from a fluoroscopic X-ray source) by use of a comparison between (a) the known object sizes sourced from first image (e.g., but not limited to, a CT image) to (b) an object measured on a second image (e.g., but not limited to, fluoroscopic image), or any combination thereof.

In some embodiments, the object size is determined from: (1) a technical specification and/or (2) the measurement on a compatible virtual image, such as, but not limited to, a rigid tool part length and/or width. In some embodiments, the method includes a tool that is designed to allow the calculation of a trajectory as a combination of depth distances from a second imaging modality camera center.

In some embodiments, the invention provides a device and a method that extend visualization capabilities of fluoroscopic imaging modality that is widely used in diagnostic and treatment medical procedures. In some embodiments, the proposed method, called herein "augmented fluoroscopy," allows enhancing visualization of a specific region of interest within the internal structures of the patient being evaluated in real time. In some embodiments, the method of the present invention is utilized for soft tissue visualization. In some embodiments, the method allows for a practitioner (e.g., but not limited to, a doctor, a nurse, a specialist, etc.) to have an increased control over the fluoroscopic visualization capabilities in medical procedures (e.g., for use in soft tissue visualization). In some embodiments, use of the method of the present invention by trainees reduces the learning curve (e.g., but not limited to, decreases training time, decreases miscalculations, etc.).

In some embodiments, the device presented in this invention includes the following functions: signal input, processing, and display capabilities, where the functions can be installed in, e.g., a procedure room. In some embodiments, the invented device is configured to integrate signals from existing imaging equipment to provide an advanced visualization capability(ies). In some embodiments, the present invention is a stand-alone device. In some embodiments, the present invention is at least one module and is integrated inside the current equipment.

In some embodiments, the method of the present invention includes performing a preoperative planning using preoperative imaging modality such as, but not limited to, a CT scan or a MRI. In some embodiments, the performed preoperative planning can be used to define the area of interest and/or mechanical properties of the tissue that can be enhanced during real-time fluoroscopy. In some embodiments, the method of the present invention, in addition to enhancement/highlighting of the area of interest on an intraoperative fluoroscopic image, can generate an overlay on an intraoperative fluoroscopic image. In some embodiments, the overlay can include: the location information of internal and external landmarks together with anatomic structures such as lesion and/or resection boundaries, incision points, bronchial airways, blood vessels, etc. In some embodiments, the method includes: (i) performing preoperative planning and (ii) using the preoperative plan during a diagnostic procedure and/or a treatment procedure. In some embodiments, use of the method of the present invention improves the efficacy and safety of diagnostic and/or treatment procedures.

In some embodiments, the present inventions disclosed herein relate to the aspects of augmented fluoroscopy device and method that allows highlighting the elements or area of interest of the fluoroscopic images in real time. Exemplary embodiments of highlighting include optional superposition (e.g., but not limited to, preoperative planning elements over static or dynamic fluoroscopic images used for diagnostic and/or treatment procedures). In some embodiments of the method of the present invention, highlighting methods include: (i) bolding a selected area, (ii) coloring a selected area (e.g., selecting an area and placing a pigment (e.g., but not limited to, yellow, blue, red, green, etc.) on a grayscale image, (iii) enhancing an image of a tissue/area (e.g., see FIG. 3, where an "augmented image" is an "enhanced image"), (iv) super-positioning a graphic over a fluoroscopic image (e.g., but not limited to, super-positioning a boundary (e.g., a dotted line, a dashed line, etc.) over a selected area of a CT scan), or any combination thereof. In some embodiments, highlighting can be performed automatically, semi-automatically, manually, or any combination thereof.

Conventional fluoroscopy is typically used to obtain real-time moving images of the internal structures of a patient during medical procedures. Conventional fluoroscopy is a visualization and validation imaging tool for guiding medical instruments inside a body (e.g., but not limited to, a human body). Although the bone tissue and medical instruments such as, but not limited to, catheters, biopsy tools, surgical instrument, calibration tool, etc., are clearly visible on a fluoroscopic image, the features of lower density matter such as soft tissue, blood vessels, suspicious nodules etc., are difficult to identify with conventional fluoroscopy. Taking lung cancer diagnostic procedures as an example, a CT scan is usually acquired, prior to procedure. While the pulmonary nodule is clearly observed on the CT scan it cannot be clearly specified on the fluoroscopic image in most of these cases. Prior to a diagnostic and/or a treatment procedure, a health care professional (e.g., a physician) typically studies a preoperative CT scan and/or a MRI image to identify the area of interest that needs to be addressed during an incoming procedure. Using the three-dimensional ("3D") imaging information and professional knowledge/experience, a physician plans the incoming procedure without an actual detailed documentation of such a plan.

During the actual diagnostic or treatment procedure physician is frequently using a fluoroscope to verify/identify the position and/or operation of the diagnostic and surgical instrument. Since the target area is not clearly specified on the fluoroscopic image, the physician can be required to guess/estimate the location of the target area. Moreover, since the fluoroscopic image represents accumulated information from the x-rays passing through the patient, as the x-rays are attenuated by varying amounts when interacting with the different internal structures of the body, the low-density soft tissues are occluded by high-density tissue. In addition, the three-dimensional information is missing from a fluoroscopic image. As a result, there is high probability of user errors caused by misinterpretation of visual information displayed on fluoroscopic images. Finally, the typical approach generally results in a the low diagnostic yield (i.e., the likelihood that a diagnostic procedure will provide the information needed to establish a definitive diagnosis) of 35%, substantially larger resection area margins (e.g., but not limited to, 10%, 20%, 30%, 40%, 50% larger), substantially longer procedure time and inconsistent results within the same medical facility while targeting soft tissue area or nodules through the conventional fluoroscopy.

An electromagnetic navigation system (ENB) may be used in the method of the present invention to support inter-body navigation. The ENB typically uses preoperative static CT images.

The method of the present invention uses real time fluoroscopic images (i.e., not static images). In some embodiments, the present invention is a device configured to achieve a real time modality that allows a user/practitioner to visualize (effectively) the soft tissue target area of diagnostic and/or treatment procedure with a diagnostic or surgical instrument. In some embodiments, real-time visualization is advantageous, since preoperative static image information, such as CT or MRI, is inaccurate for localization of instruments relatively to the target area due to significant movement and/or deformation of the lung tissue during breathing, where deformation is caused by an advancement of a diagnostic instrument or a surgical instrument inside a patient (e.g., a human body) in addition to potentially substantially dissimilar patient conditions compared between (a) a preoperative CT imaging and (b) actual diagnostic or treatment procedure.

In some embodiments, the method of the present invention can include use of a third imaging modality configured to use a second imaging modality (e.g., but not limited to, real time fluoroscopy) during a diagnostic treatment or a treatment procedure in conjunction with use of a first imaging modality (e.g., but not limited to, preoperative CT). In some embodiments, the method can include a third imaging modality configured to produce a third image having highlighted elements/features of interest (i.e., augmented image) during a diagnostic and/or a surgical procedure. In some embodiments, the method can facilitate a reduction in operation time and/or an improvement in the learning curve of such procedures (e.g., for a nascent practitioner).

In some embodiments, the method of the present invention can be used during a surgical procedure and/or guiding under real-time visualization of an area of interest.

In some embodiments, the method allows a practitioner to control visibility of specific elements of an area of interest on a third image (e.g. fluoroscopic image) by adding at least one three-dimensional aspect of information to a second image (e.g. conventional fluoroscopic image). In some embodiments, the method can aid a user to focus on an area of interest (i.e., the correct area of interest required during a surgical procedure), including, for example, an inspection of adjunctive structure around the area of interest, such as, but not limited to, blood vessels, bronchial airways, etc. In some embodiments, the method of the present invention includes suggesting to a user an optimal fluoroscopic angle to increase visibility of a lesion at the time of a diagnostic and/or treatment procedure, where the suggestion is based on at least one DDR preoperative image.

In some embodiments, the method of the present invention allows for providing increased control to a physician during a surgical procedure, where the control includes sufficiently improving the physician's ability to accurately identify a treatment area and/or at least one critical structure(s) relatively to the diagnostic instrument and/or surgical instrument according to pre-operative planning and three-dimensional imaging data.

In some embodiments, the method of the present invention uses a hardware device having integrated software algorithms that are configured to allow for an integration and processing of first images (e.g. pre-procedure) and second images (e.g. intraoperative fluoroscopic), and rendering real-time or offline images of a third image (e.g. augmented fluoroscopy) on an output (i.e., a result).

In some embodiments, the method of the present invention uses an angular measurement device/sensor (e.g., a right angle sensor, an accelerometer, gyroscope, etc.) that is configured to allow for determining a spatial relative angle and/or position (pose) between: (a) the C-Arm of fluoroscope and (b) the patient.

In some embodiments, the method of the present invention can utilize a steerable catheter configured to allow measuring a depth inside a patient (e.g., but not limited to, within a patient's chest) and/or a distance from a fluoroscopic camera.

In some embodiments, the device and method of the present invention provide a real-time third imaging modality (e.g. augmented fluoroscopic modality) to allow for use of (a) information originated from a first image (e.g. preoperative CT image) and (b) information (e.g., decisions) made during the planning phase for highlighting an area of interest (i.e., providing an augmented image), optionally including a display of (a) the information originated from the first image and/or (b) information generated during the planning phase over second image (e.g. fluoroscopic image).

In some embodiments, the methods of the present invention can be used to assist the diagnostic and/or treatment procedures involving soft moving tissues such as, but not limited to, lung, liver, kidney, etc. In an exemplary embodiment, in pulmonology, peripheral nodules can be highlighted on a fluoroscopic image and/or a digitally reconstructed radiograph (DRR) image of the peripheral nodules can be superimposed over the fluoroscopic image in real time. In some embodiments, the approach of using three-dimensional CT image to highlight the area of interest on the two-dimensional ("2D") fluoroscopic image is applicable to other medical applications.

In some embodiments, the method of the present invention can be used with a Cone Beam CT device. In some embodiments, combining the method of the present invention with a Cone Beam CT device allows for greater navigation accuracy, automatic fluoroscopic pose control, radiation dose reduction, etc.

In some embodiments, the method of the present invention allows a practitioner to navigate and/or operate a medical instrument(s) according to real time information highlighted on third image (e.g. fluoroscopic image/augmented image), where the third image can include superimposed anatomical and/or planning data extracted from a pre-operational image.

In some embodiments, the method of the present invention provides a real-time third image (e.g. fluoroscopic image/augmented image) of an actual surgical instrument and highlighted area of interest and/or anatomical elements. In some embodiments, the method can provide an overlaid targeted anatomical feature(s) on the augmented image. In some embodiments, the method can provide planning information, such as, but not limited to, incision points, cutting area boundaries, reference points, etc., on the augmented image.

In some embodiments, the method and device of the present invention allow a user/practitioner to combine multimodal imaging information and utilize previously acquired three-dimensional volume data to highlight moving and static soft tissue area (i.e., generate an augmented image).

In some embodiments, the method of the present invention includes producing an augmented fluoroscopy image that provides to a user/practitioner an identifying structure(s) on the augmented fluoroscopic image, which is generated by a movement variability analysis of groups of pixels (e.g., different groups of pixels) on a fluoroscopic video and/or sequential fluoroscopic image(s). In an exemplary embodiment, the soft tissue lesion inside the lungs moves in a different direction in comparison with the ribs, and the amplitude of soft tissue movement is typically greater than one of the ribs, resulting in a projected movement of the soft tissue and rib structures having a difference as measured by the fluoroscopic video frames. In some embodiments, the measured difference combined with the information of each pixel attenuation value allows for the grouping of pixels into physical structures and/or objects. In some embodiments, when grouped into objects, the physical structures can be highlighted or deemphasized on the fluoroscopic image in reference to a medical application determined by a user/practitioner. In some embodiments, the augmented fluoroscopic image can be further enhanced by extracting the object information from the sequence of fluoroscopic images, which can be optionally refined with the information provided by a preoperative image such as, but not limited to, CT, MRI, chest x-ray radiographic image, or any combination thereof.

In some embodiments, the method of the present invention includes an automatic calibration of at least one static fluoroscopic image and/or video frame from a real time video. In another embodiment, the method includes (i) generating a prediction of the quality of specific anatomical structure or visibility of an area of interest during intraoperative fluoroscopy at various angles and (ii) recommending angles to use a fluoroscopic C-Arm for improving visibility of the specific anatomical structure or area of interest, which provides guidance to a user and achieves increased visibility of the structure/area of interest, e.g., relative to the background of an image.

In some embodiments, the method of the present invention provides processing the RAW data obtained from a fluoroscopic device by changing an existing automatic gain algorithm integrated with the fluoroscopic device, based on the whole fluoroscopic image. In some embodiments, the method includes the use of a region-based gain calculation algorithm. In some embodiments, a specified region-based gain calculation algorithm is derived from the knowledge of correspondent three-dimensional anatomy, where the correspondent three-dimensional anatomy is obtained from CT or MRI images, around the area of interest and includes evaluating the physical properties of the area of interest. In some embodiments, the method provides for a specific signal processing, which reduces a loss of information provided on the resulting fluoroscopic image in the target area (i.e., augmented image), and can also resulting in an increase of visibility of the target area.

In some embodiments, the method and device of the present invention can be used to maintain/generate an accurate registration (i.e., coarse registration and/or fine registration) between two or more operative real-time video images and/or static preoperative images.

In some embodiments, the method and device of the present invention can include the use of pre-operative data (i.e., decisions/information generated by a user/practitioner), where information is displayed on the screen, and the resolution and/or quality of the displayed information can be dynamically determined on an application-specific or user-specific basis.

In some embodiments, the present invention is a method that uses a hardware device having integrated software algorithms configured to provide an input from a first imaging modality (e.g. pre-procedure image) and second imaging modality (e.g. intraoperative fluoroscopic image) that generates third imaging modality images (e.g. augmented fluoroscopic image) as output.

In some embodiments, the method of the present invention provides a real-time output calibrated image with configurable display elements and output video format.

In some embodiments, the method of the present invention can use a hardware device with integrated software algorithms that has standalone and/or modular architecture.

In some embodiments, the method of the present invention uses a hardware device that is configured to provide an angular measurement determining relative spatial pose between the fluoroscope C-Arm and patient body to a user. In some embodiments, the device is applicable for those fluoroscope models where the angular information is unavailable or inaccessible during procedure.

In another embodiment, the method of the present invention can include reconstructing at least one anatomical structure in a three-dimensional space from several fluoroscopic images (e.g., 2 images, 3 images, 4 images, 5 images, 6 images, 7 images, 8 images, 9 images, 10 images, etc.) by using the correspondent three-dimensional anatomical structures derived from preoperative images, e.g., CT scans).

Referencing FIG. 1 there is shown a flowchart that illustrates method 100 of an embodiment of the present invention.

At 101 of the method 100 of an embodiment of the present invention, first image (e.g. preoperative image, such as CT or MRI), is acquired and transformed into 3D space, which is used during surgical treatment or diagnostic procedure to plan the treatment and/or diagnosis.

At 102 of the method 100 of an embodiment of the present invention, the practitioner (for example, but not limited to, pulmonologist or surgeon) performs pre-procedure planning on the pre-procedure data acquired at 101, during which the practitioner marks the area of interest (e.g., the boundaries of the area to biopsy or resect around the suspicious lesion, the approach or incision points for preferred tool introduction, critical structures (e.g., but not limited to, major blood vessels, restricted area)), the preferred pathway to approach the area of interest. In some embodiments, the procedure (i.e., 102) may be performed manually and/or semi-automatically, such as when part of information is automatically identified by computer software.

In some embodiments of the present invention, once the planning is completed, at 104 the information is processed to map (i.e., "mapping") and/or identify (i.e., "identifying") the area of interest, where mapping and/or identifying allows for planning elements in a 3D space and/or identify major anatomical structures. In some embodiments, information gathered from mapping (i.e., "mapping information") is transferred from (a) image sourcing from a first imaging modality to (b) an image sourcing from a second imaging modality. In some embodiments, the mapping information is transferred after the coarse and/or fine registrations are performed on the first image source and the second image source. In some embodiments, an image source (e.g., but not limited to, a first image source) can be use/reused for highlighting purposes during second imaging modality operation (e.g., but not limited to, intraoperative fluoroscopy).

Non-limiting examples of mapping or identifying techniques for body organs are disclosed in "Automatic localization of solid organs on 3D CT images by a collaborative majority voting decision based on ensemble learning" by Zhou X, Fujita H, Comput Med Imaging Graph, 2012, which is herein incorporated by reference in its entirety. For example, a location of a target organ in a 3D CT scan can be presented as a 3D rectangle that bounds the organ region tightly and accurately (e.g., serving as a boundary for at least one organ). For example, the location of a target organ-specific 3D rectangle (e.g., but not limited, to a bound rectangle) is detected automatically. Multiple 2D detectors are trained using ensemble learning and the outputs of the multiple 2D detectors are combined using a collaborative majority voting in 3D to localize an organ(s). For example, the location detection of different inner organs can be used separately and/or independently. The exemplary method includes treating 3D organ localization in a 3D CT scan as detecting several independent 2D objects in a series of 2D image slices, where the method can (i) reduce the feature dimension (3D to 2D) and (ii) increase the number of training samples (e.g., one 3D training sample consists of a large number of 2D training samples) during ensemble learning. The exemplary method can increase the robustness of the trained detector for unknown samples according to Occam's razor. For example, for an unknown 3D CT scan, the exemplary method applies different 2D detectors to each voxel independently to detect a number of 2D candidates of a target along three orthogonal directions and votes those 2D candidates back to the 3D space. The existence and approximate center position of the target can be determined by checking the mutual consent of the responses all 2D detectors and selecting the majority of the range of the related 2D candidates in the 3D voting space as the target location.

Non-limiting examples of mapping or identifying techniques for body organs are also disclosed in "Registration of a CT-like atlas to fluoroscopic X-ray images using intensity correspondences," M. Sc thesis by Aviv Hurvitz, supervised by Prof. Leo Joskowicz, The Rachel and Selim Benin (School of Computer Science and Engineering The Hebrew University of Jerusalem, Israel, August, 2008), which is herein incorporated by reference in its entirety. This exemplary method allows for intraoperative localization of bones, where the method does not require any preoperative images, and is less invasive than many alternatives. For example, in the preoperative stage, a CT-like intensity atlas of the anatomy of interest is constructed from sample CT images. In the intraoperative stage, a novel 2D/3D deformable registration algorithm is used to register the atlas to Fluoroscopic X-ray images of the patient anatomy. The registration algorithm is configured to establish intensity-based correspondences between the atlas's template bone surface and bone contours in the fluoroscopic X-ray images. The registration algorithm further is configured to search for the bone shape and pose that minimize/reduce the distances between paired features. The algorithm iteratively is configured to refine the bone shape and pose estimates until the bone shape and the pose estimate(s) converge.

In some embodiments, the method includes generating an augmented 3D fluoroscopic image by use of a 2D fluoroscopic image by matching each pixel on the 2D fluoroscopic image to 3D structures sourced from a CT scan. The method of the present invention does not utilize tracing elements and/or markers, such as, but not limited to, radiopaque marker tethered to a device, a radiopaque particulate spray, an inflatable radiopaque balloon, a radiopaque filament, during a registration.

In embodiments, the method of the present invention can generate: (i) visualization data that shall be displayed during surgical procedure; (ii) a recommended pathway for introduction of at least one medical instrument; (iii) guidance instructions based on anatomic knowledge and procedure details; (iv) recommended angles or pose for C-Arm, as to result in optimizing the area of interest visibility, or any combination thereof.

In some embodiments, the fluoroscopic image is acquired at 106 during procedure while medical instrument is introduced into the area of interest. In some embodiments, the fluoroscopic image can be acquired as single image and/or video.

Figure 2:
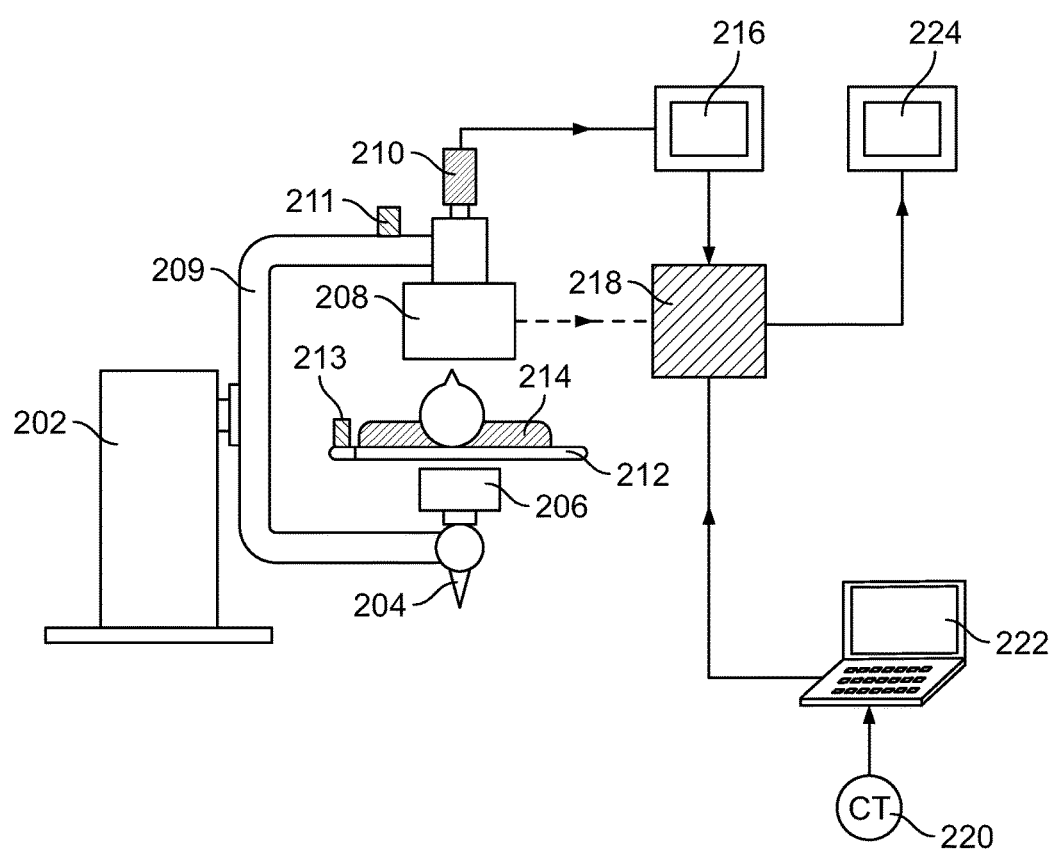
FIG. 2 is an illustration of an embodiment of the method of the present invention (e.g., showing an augmented fluoroscopy system and data flow).

In an embodiment, the generated fluoroscopic image and/or video is introduced into the processing unit 218, FIG. 2 as an input for fluoroscopic image processing 108. In the embodiment, the pose between the Fluoroscopic C-Arm 209, FIG. 2 and patient 214, FIG. 2 is either transmitted from outside or calculated by processing unit. In the embodiment, the compatible digital reconstructed radiograph (DRR) image is generated from a pre-procedure image using substantially the same pose of a virtual C-Arm and substantially the same camera parameters as the actual Fluoroscope. In some embodiments, the image is calibrated, where "calibrated" means being adjusted for fluoroscopic image distortion and compensated for x-ray energy difference between the fluoroscope and CT at the intensity values according to the prior art knowledge of X-ray radiometry.

In some embodiments, the following references discuss DDR simulation, calibration and registration to actual fluoroscopic images: "2D/3D Image Registration on the GPU." Alexander Kubias, University of Koblenz-Landau, Koblenz, Germany, Thomas Brunner, Siemens Medical Solutions, Forchheim, Germany, 2007, which is hereby incorporated by reference in its entirety. For example, this exemplary method performs the rigid 2D/3D image registration efficiently on the GPU [graphics processing unit]. Both parts of the registration algorithm, i.e. the DRR generation and the computation of the similarity measure, are executed on the GPU. Additionally, "2D/3D Registration for X-ray Guided Bronchoscopy using Distance Map Classification," by Di Xu, Sheng Xu, Daniel A. Herzka, Rex C. Yung, Martin Bergtholdt, Luis F. Gutiérrez, Elliot R. McVeigh, is hereby incorporated by reference in its entirety. For example, the registration algorithms can be grouped into two categories: (1) intensity based and (2) feature based, where the feature-based registration can be used in connection with the method of the present invention. For example, the edges of the ribs and spine can be extracted from the X-ray and/or CT images. A distance map can further be generated for a plurality of (e.g., but not limited to, each recorded edge point, which can result in using all edge points) the edge points of the X-ray image to facilitate/allow the 2D/3D registration by attracting the edge projections of the CT image to the closest edges in the X-ray image. When the distance map does not have any orientation information of the edges, mis-registration can occur between the edges of different structures. Mis-registration can be reduced by using orientation dependent distance maps to achieve more robust registration with improved capture range and accuracy.

In some embodiments, the map generated in 104 is used to provide spatial information for each projected element on the DRR image. In some embodiments, the registration is performed between DRR and actual fluoroscopic images. Examples of registration, e.g., feature-based or intensity-based registration, are described in "Automatic registration of portal images and volumetric CT for patient positioning in radiation therapy", (See, e.g., Ali Khamene, Frank Sauer, Medical Image Analysis 10 (2006) 96-112), which is hereby incorporated by reference in its entirety. For example, the feature based registration approach can involve a step of feature correspondence between features of each of the imaging modalities participating in registration process. As a result of the registration the spatial information generated for DRR image can be transferred onto the actual fluoroscopic image. The 3D spatial information added to the actual fluoroscopic image allows implementing computer vision approach to the actual fluoroscopic image, thus operating with objects in 3D space rather than working with 2D image of pixels. Using this approach allows for each pixel of a fluoroscopic image to be described by integration of X-ray beam passing through known anatomic structures.

In some embodiments, the information that was lost during fluoroscopic image acquisition is restored using the method of the present invention. In some embodiments, the area of interest can be highlighted on the actual fluoroscopic image, while the interfering structures such as bones, heart, blood vessels can be deemphasized. In some embodiments, an additional improvement of the augmented image quality can be achieved through the tracking of sequential video frames, where the movement characteristics may vary for different anatomic structures.

The augmented fluoroscopic image or video frame sequence is produced in 110 using an embodiment of the method of the present invention. In some embodiments, various elements generated on the planning phase can be displayed on augmented fluoroscopic image according to user demand or depending on system configuration.

FIG. 2 shows a diagram illustrating an embodiment of the present invention, showing an augmented fluoroscopy system/method and data flow.

In an embodiment of the present invention for producing an augmented fluoroscopic image, the method included use of:

1) C-Arm 202 that is responsible for movement of frame 209 with attached fluoroscopic pair of X-Ray tube 204 and intensifier 208;
2) X-Ray tube 204 that generates X-rays, passing through the collimator 206, that is designed to narrow the X-ray beams;
3) the generated X-ray beam is passing through the patient body 214 attached to the bed 212;
4) the attenuated X-Ray beam is further absorbed by X-ray image intensifier 208 forming the RAW data fluoroscopic image. The X-ray is converted into the visible image by 208; and/or
5) the video signal is constantly captured by camera 210 and transferred to the monitor 216.
6) a planning station 222 that is getting CT image 220 as an input allows user to plan diagnostic and treatment procedure as specified by 102, 104 FIG. 1 above;
7) a generated planning data, 3D volume data are transferred into unit 218, where a video signal from 216 or alternatively RAW data from 208 is constantly transferred to the processing unit 218;
8) the augmented video image is produced by 218 as specified by 108, 110 FIG. 1 and displayed by the monitor 224;
9) or any combination thereof.

In an embodiment of the present invention, the following elements were added to provide the C-Arm pose measurement: (1) a sensor 211 attached to frame 209 of C-Arm and/or (2) a reference sensor 213 attached to the patient body 214 and/or to patient bed 212.

Examples of sensing technologies available for use in embodiments of the present invention to allow for evaluation of pose estimation can include: an optical sensor, an accelerometer, an electro-magnetic sensor, an ultra-sonic sensor, a gyroscopic sensor (e.g., available on the modern smart phones), etc. An example of use of a pose estimation approach, which can be used in the method of the present invention, is described in "Robust Multi Sensor Pose Estimation for Medical Applications" by Andreas Tobergte, Gerd Hirzinger, Intelligent Robots and Systems, 2009, IROS 2009, IEEE/RSJ International Conference, which is hereby incorporated by reference in its entirety.

In some embodiments, the method can use a set(s) of markers with predefined geometric configuration can be attached to the patient bed as discussed in "Fast Marker Based C-Arm Pose Estimation" by Bernhard Kainz, Markus Grabner, and Matthias Rüther, Institute for Computer Graphics and Vision, Graz University of Technology, Austria, which is hereby incorporated by reference in its entirety.

FIG. 3 shows an exemplary embodiment of the present invention, showing an illustration of an augmented fluoroscopic image. In an embodiment, the diagnostic instrument and bones are clearly seen on the original image while the target area is invisible or unclear. In an embodiment, the target area is highlighted on the augmented fluoroscopic image, e.g., on the right. In an embodiment, the method includes highlighting blood vessels, while deemphasizing the bones.

Figure 4:
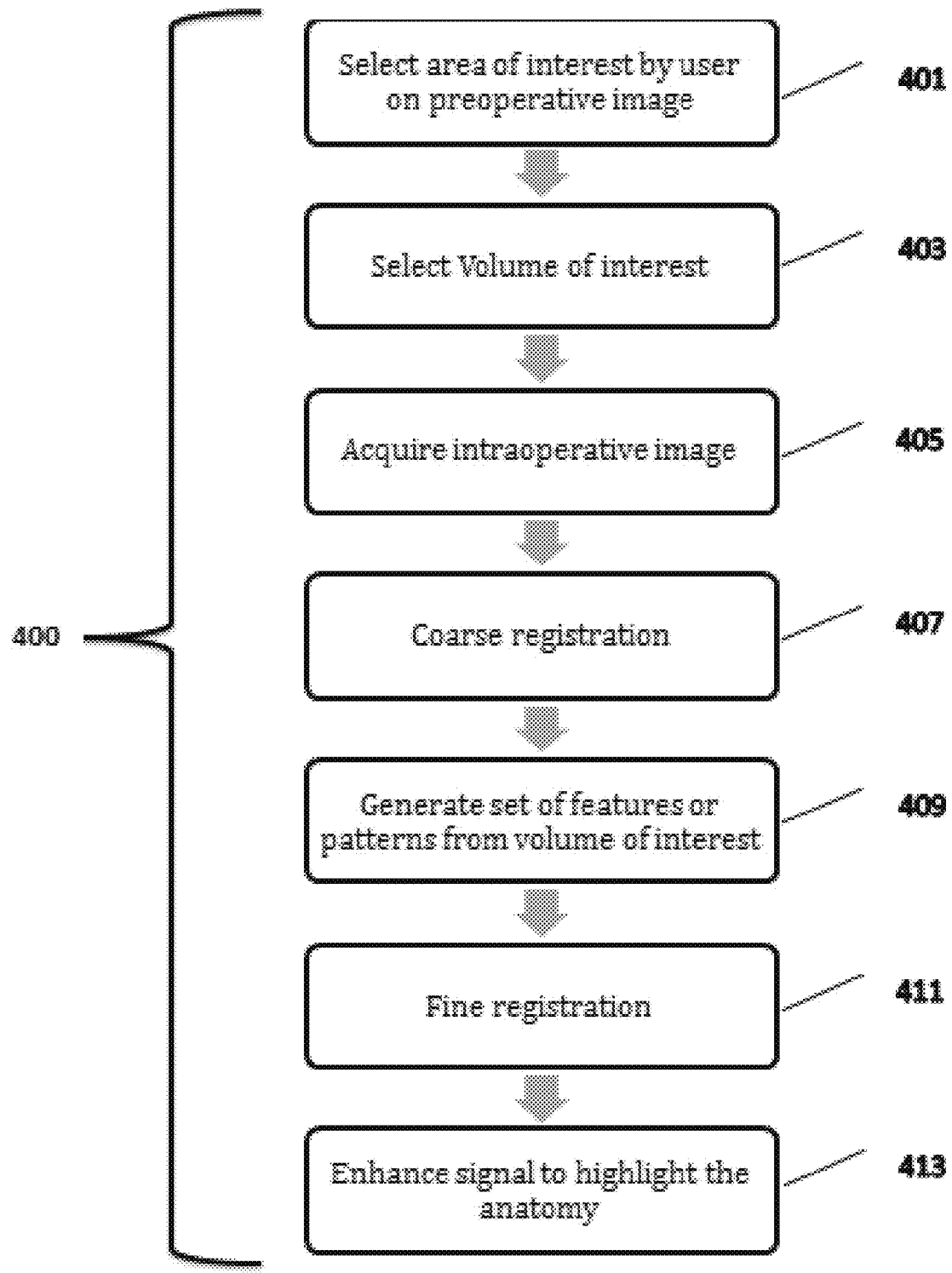
FIG. 4 is a flow chart showing an embodiment of the method of the present invention (e.g., an anatomical structure enhancement flow chart).

FIG. 4 shows an embodiment of the method of the present invention, showing a flowchart of the method 400. At 401 of the method 400 shows an area of interest being selected by user on preoperative image, such as CT or MRI prior to diagnostic or treatment procedure. At 403 of the method 400, the volume of interest is generated on preoperative image. In an embodiment, the volume is generated in such way that the anatomical structures in the area of interest, such as lesion, and adjunctive anatomical structures such as bronchi or blood vessels, will be detectable on operative image, such as fluoroscopic image. In an exemplary embodiment, for instance, DDR image can be used to evaluate detectability on fluoroscopic image.

In some embodiments of the method of the present invention, at 405 of method 400, intraoperative image or videos are acquired. In an embodiment, the pose of the intraoperative modality is calculated or recorded with at least one intraoperative image. In an embodiment, at 407 of the method 400, the coarse registration between intraoperative and preoperative images is performed, e.g., but not limited to, fluoroscopy to DDR, to evaluate a viewpoint of DDR inside a preoperative image data, such as, but not limited to, CT volume. An example of coarse registration is shown in "2D/3D Image Registration on the GPU," by Alexander Kubias, University of Koblenz-Landau, Koblenz, Germany, Thomas Brunner, Siemens Medical Solutions, Forchheim, Germany, 2007, which is hereby incorporated by reference in its entirety. Some embodiments of the method of the present invention use, for example, a rib-based rigid image registration: For example, using 2D/3D image registration, a preoperative volume (e.g. CT or MRT) is registered with an intraoperative X-ray image. Rigid image registration can be used by the method of the present invention, where a volume can only be translated and rotated according to three coordinate axes, where a transformation is given by the parameter vector $x=(t_x, t_y, t_z, r_x, r_y, r_z)$. The parameters $t_x$, $t_y$, $t_z$ represent the translation in millimeters (mm) along the X-, Y- and Z-axis, whereas the parameters $r_x$, $r_y$, $r_z$ belong to the vector $r=(r_x, r_y, r_z)$. In some embodiments, coarse registration can be performed automatically.

In some embodiments, the method of the present invention can use the registration techniques disclosed in, "Automatic registration of portal images and volumetric CT for patient positioning in radiation therapy," by Ali Khamene, Frank Sauer, Medical Image Analysis 10 (2006) 96-112, which is hereby incorporated by reference in its entirety. In exemplary embodiments, such registration can be implemented, as a non-limiting example, as intensity-based and/or as feature based, depending on the specific medical application. Examples of intensity-based and feature based registration are described by "Intensity-based Registration versus Feature-based Registration for Neurointerventions" by Robert A., David J. Hawkesb, Medical Vision Laboratory, Dept of Engineering Science, University of Oxford, England, which is hereby incorporated by reference in its entirety.

In some embodiments of the method of the present invention, point-based registration can be implemented using known anatomical landmarks on a patient's chest. In some embodiments, at least one known landmark(s) can be marked on a CT image and/or fluoroscopic image. In some embodiments, special markers can be attached to the patient's chest during procedure to improve/increase detectability on a fluoroscopic image.

In some embodiments, at 409 of the method 400, the set of features or patterns, depending on desired registration method, is generated from a volume of interest of the preoperative image. In some embodiments, when the soft tissue structures of a patient are observed and move relative to the ribs of the patient, the viewpoint calculated during coarse registration at 407 is approximated within the known tolerance. In some embodiments, the set of patterns generated at 409 will allow performing the fine-tuning (i.e., fine registration) of the viewed area in the following step.

In some embodiments, at 411 of the method 400, fine registration is implemented to find the best fit between each of the features or patterns, depending on the registration method, generated at 409 and area of interest on intraoperative image.

Figure 5A:
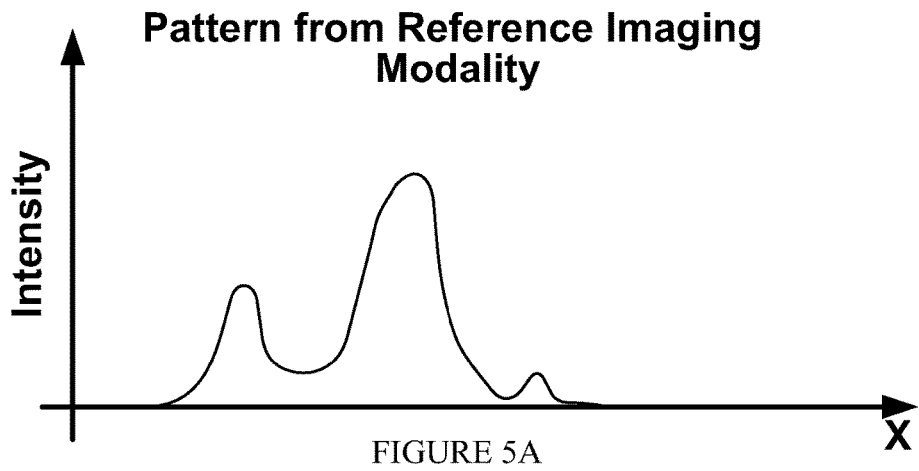
FIG. 5 is an illustration showing an embodiment of the method of the present invention, illustrating three intensity measurements of the method of the present invention: (A) shows a pattern obtained from a reference imaging modality; (B) shows a signal from an intraoperative modality; and (C) shows an augmented signal from intraoperative modality. This illustration shows an embodiment of the method of the present invention, where the intensity measurements can be used for fine registration (i.e., template matching), based on at least one signal enhancement.
Figure 5B:
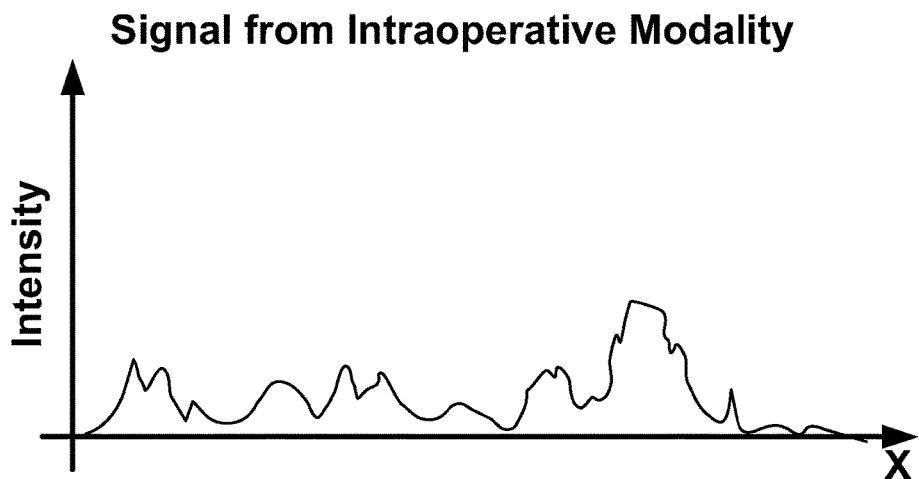
Figure 5C:
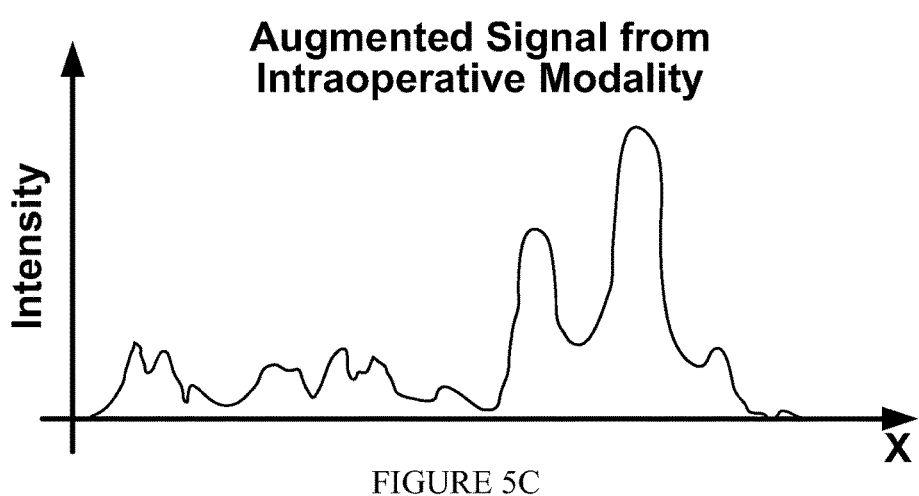

In an exemplary embodiment, a fine registration method is illustrated through intensity-based fine registration (i.e., template matching), e.g., as shown in FIG. 5, where the approach is initiated with an intensity-based pattern, as shown in FIG. 5A, from a pre-operative or a reference imaging modality. In an embodiment, the signal from an intraoperative image, as shown in FIG. 5B, contains noise and scale corresponding to the pattern shown in FIG. 5A, and is measured within the area of interest. In an embodiment, the pattern shown in FIG. 5A is matched to the pattern from signal FIG. 5B.

An example of a fine registration (i.e., template matching) technique that can be used by the method of the present invention is described in: "An Overview of Template Matching Technique in Image Processing" by T. Mahalakshmi, R. Muthaiah and P. Swaminathan School of Computing, SASTRA University, Thanjavur, Tamil Nadu, India, Research Journal of Applied Sciences, Engineering and Technology 4(24): 5469-5473, 2012., which is hereby incorporated by reference in its entirety. Some embodiments of the method of the present invention use an area-based approach, which are also referred to as correlation-like methods or fine registration (i.e., template matching), see, e.g., Fonseca and Manjunath, "Registration techniques for multisensor remotely sensed imagery" PE & RS-Photogrammetric Engineering & Remote Sensing 62 (9), 1049-1056 (1996), which describes the combination of feature detection and feature matching. For example, this method is suited for the templates which have no strong features corresponding to an image, since the templates operate directly on the bulk of values. Matches are estimated based on the intensity values of both image and template. Techniques that can be used by the method of the present invention include: squared differences in fixed intensities, correction-based methods, optimization methods, mutual information, or any combination thereof. In some embodiments, the method of the present invention can perform a fine registration automatically.

In some embodiments, the method of the present invention can perform a coarse registration automatically.

In an exemplary embodiment, the method of the present invention can utilize a fine registration method, where the fine registration method includes aligning a 2D projection of an anatomical structure from a CT scan obtained through coarse registration with correspondent anatomical structure extracted from fluoroscopic image.

At 413 of the method 400 of an embodiment of the present invention, the signal matching pattern is shown in FIG. 5A. Inside the signal (FIG. 5B) is enhanced to highlight the anatomy found in the area of interest as drawn by 401. In some embodiments, in addition to highlighting the signal from intraoperative image, the signal sourcing from reference image can be overlaid on the display/image. In another embodiment, the combination of original signal from intraoperative image, simulated signal from reference image and planning information can be displayed according to application configuration or upon the user request. In some embodiments, the method shown in FIG. 5C can be alternatively used for signal suppression.

FIG. 5 shows an illustrative example of fine registration (as shown in step 411 of FIG. 4) (i.e., template matching) of the method of the present invention. Although this illustration is shown in one dimension for simplicity purposes, the original signals of the embodiment are two-dimensional. In some embodiments, steps 411 and 413 of FIG. 4 provide the methods using a template-matching registration approach.

Figure 6A:
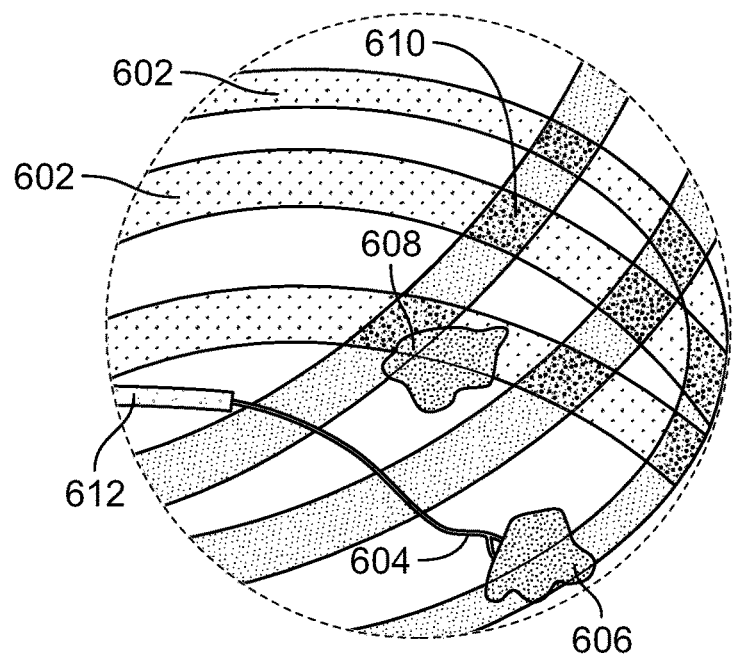
FIGS. 6A and 6B is a schematic drawing showing an embodiment of the method of the present invention, illustrating a fluoroscopic image.
Figure 6B:
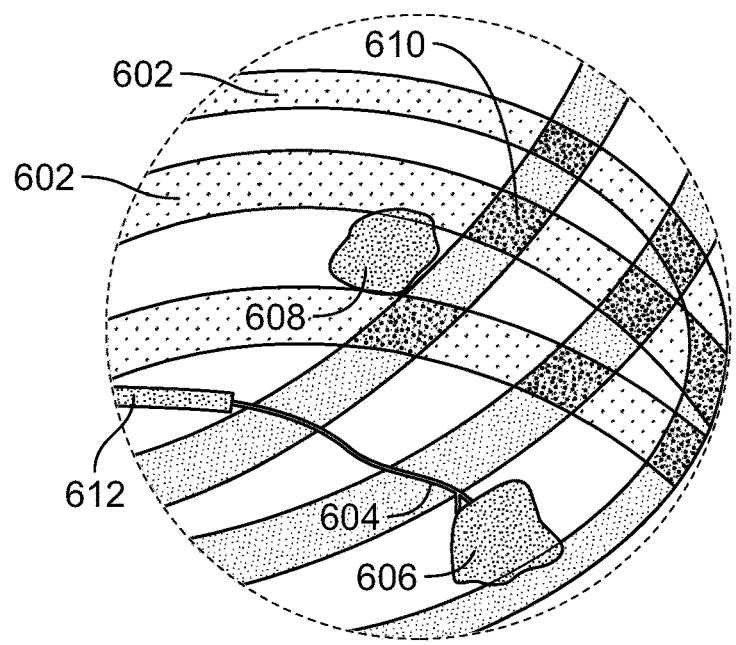

The exemplary embodiment shown in FIG. 6, is a schematic drawing of a fluoroscopic image, where A, FIG. 6 and B, FIG. 6 represent fluoroscopic images for two different lung positions during breathing. In the embodiment, the ribs 602 remain almost static while the soft tissue lesions 606 and 608 move substantially between the two breathing positions. In an embodiment, the tip of the forceps 604 is located in the close proximity of lesion 606, which results in the forceps moving with the lesion 606, while the bronchoscope 612, which is located far from the lesion, is substantially static and does not substantially move between two breathing positions A and B. In an embodiment, the rib intersection area 610 is darker then the rib 502 and can be potentially confused with lesion on the conventional fluoroscopic images. In some embodiments, the analysis of sequential fluoroscopic images A and B allows to separate substantially static and moving objects, group the static and moving objects by (i) movement, (ii) connectivity, (iii) density, or any combination thereof, and/or perform reconstruction of anatomic structures from a plurality of fluoroscopic images.

In some embodiments, the inventive method can be used for the following pulmonology-based procedures including, but are not limited to:

1) Endobronchial diagnostic biopsy, when the pulmonologist first identifies the lesion under augmented imaging. Then, the biopsy forceps are advanced to the target site under augmented imaging to insure the biopsy is taken appropriately;
2) Augmented imaging guided percutaneous diagnostic biopsy;
3) Wedge resection with VATS or thoracotomy when thoracic surgeon places markers augmented fluoroscopy guidance prior to surgical procedure;
4) Trans-bronchial needle biopsy direct vision is used to visualize the lesion and to guide the bronchoscope. The area to be biopsied is first identified under augmented imaging and then the scope is advanced as far as possible to the targeted segment. Using augmented imaging helps to guide the forceps distally to the target area, beyond the range of direct vision;
5) Augmented imaging guided endobronchial or percutaneous ablation;
6) Or any combination thereof.

In some embodiments, the present invention is used to generate multidimensional images from 2D fluoroscopic images. In some embodiments, a 2D fluoroscopic image is displayed in gray levels and comprised of pixels. In some embodiments, each pixel represents an integrated density of at least one tissue while an x-ray generated by an x-ray tube is absorbed by an image intensifier.

In some embodiments, the objects of higher density (e.g., bones and blood vessels) have greater weight on the integrated pixel density (color) in comparison with integrated pixel density of, e.g., air and/or soft tissue. In some embodiments, automatic gain algorithms implemented for fluoroscopic devices make at least one high-density tissue visible while reducing the visibility of at least one soft tissue. In some embodiments, at least one suspicious lesion area, although having small volume relative to, e.g., bones, has higher tissue density than at least one normal tissue. In some embodiments, at least one suspicious lesion area is characterized by increased blood activity (e.g., flow and/or volume) in comparison to at least one area around normal tissue. In some embodiments, at least one natural anatomic characteristic of a suspicious lesion area (e.g., in soft or dense tissue), includes at least one shadow and/or cloud-like object observed by at least one fluoroscopic image. In some embodiments, there are additional sources for the at least one shadow and/or cloud-like object by at least one fluoroscopic image (e.g., at least one rib cross-section, joint, major blood vessel, etc.)

In some embodiments, the present invention is a method that separates at least two different (e.g., non-identical) portions of visible tissue(s) (which can be the same or different tissue) on a fluoroscopic image and combines the at least two different portions into objects through segmentation and tracking of visible tissues using optical flow on fluoroscopic video. In some embodiments, the pixels on a fluoroscopic screen are (1) classified by density range, (2) tracked through the live fluoroscopic video, and (3) classified by movement. For example, breathing includes lung expansion and contraction movements, which vary from lobe to lobe in the same lung and also vary from movement of ribs. Such movements result in a lung projection, and can be shown by the fluoroscopic video images generated from the inventive method of the present invention, characterized by a plurality (e.g., a variety) of movements for every distinguishable anatomical structure as illustrated by FIG. 6.

In some embodiments, the method of the present invention includes a registering process/step, where the registering process/step uses as input: a segmentation of bronchial airways from (i) a fluoroscopic image and (ii) a CT scan. In some embodiments, a course and/or fine registration is performed using a registering step.

Figure 7:
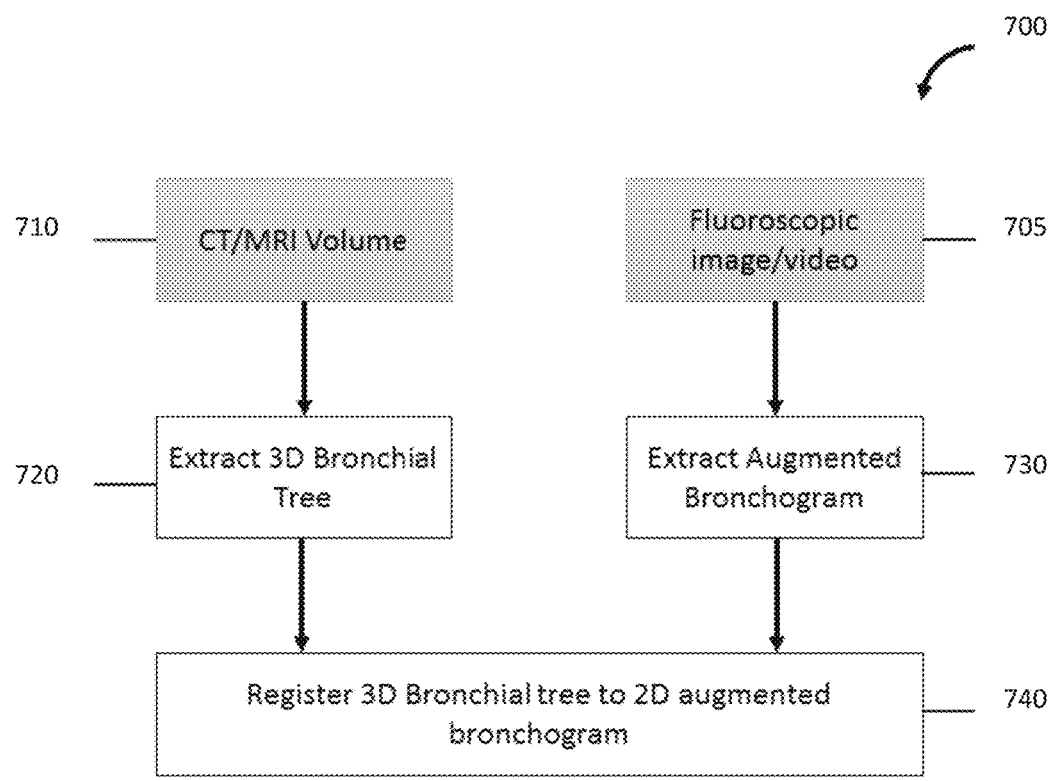
FIG. 7 is an embodiment of the method of the present invention, illustrating a registration step using (1) information pertaining to a bronchial airway tree, where the information is extracted from a preoperative image (e.g., a 2-dimensional or a 3-dimensional image; e.g., a CT scan) and (2) information pertaining to at least one airway, where the information is extracted from a fluoroscopic image(s) by use of an augmented bronchogram.

In some embodiments, a method allows registration between at least one bronchial airway tree extracted from a preoperative CT image and airways extracted from fluoroscopic image sequence using augmented bronchogram. In an embodiment, a general flow is illustrated in FIG. 7.

In some embodiments, the present invention is an augmented bronchogram. In some embodiments, the augmented bronchogram is an augmented image of invisible airways (e.g., not visible by fluoroscopic image) and is extracted from fluoroscopic images.

Figure 8:
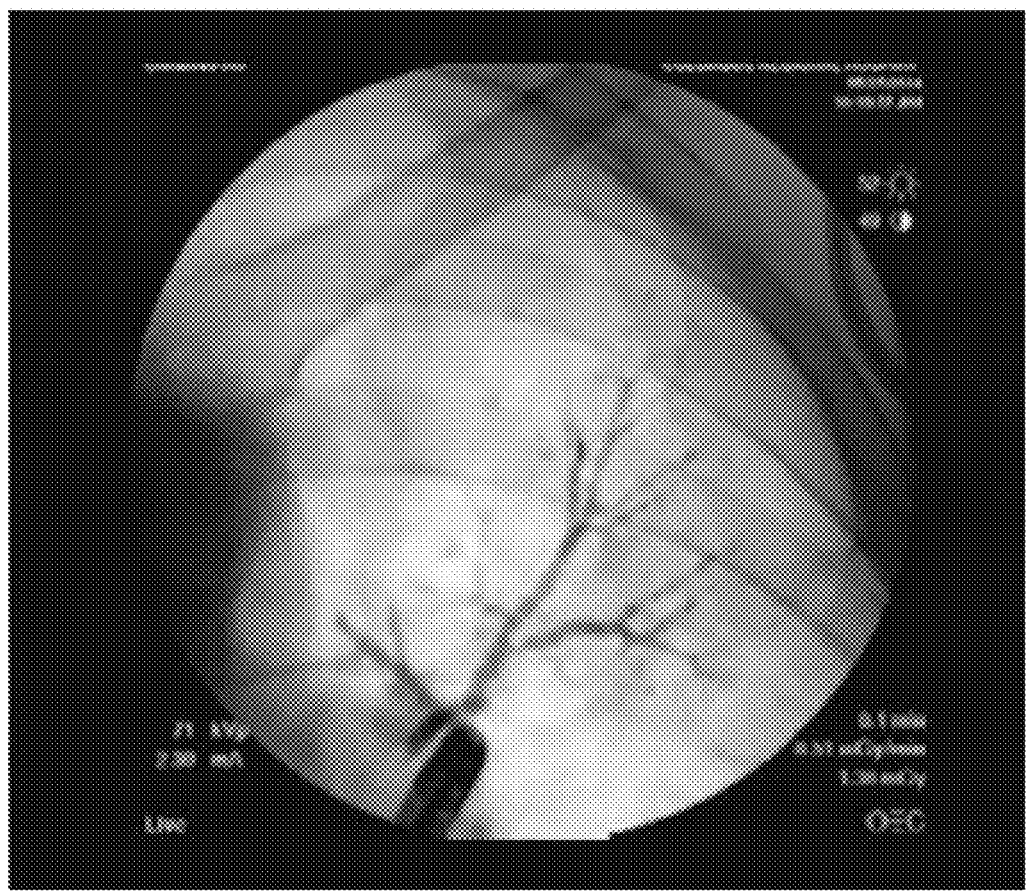
FIG. 8 shows an embodiment of the method of the present invention, illustrating a fluoroscopic image directly after injecting (e.g., 0 seconds after injecting) an area with a radiopaque substance.

In an embodiment, an augmented bronchogram is generated by injecting a radiopaque substance configured to make bronchi visible (FIG. 8). In an embodiment, visible bronchi provide information (1) to extract a partial bronchial tree from fluoroscopic images and (2) to register the partial bronchial tree to a second image, e.g., the bronchial tree extracted from a preoperative image. In some embodiments the radiopaque substance injected in bronchi does not highlight (i.e., make visible) the airways uniformly. In some embodiments, the radiopaque substance quickly disappears from an image or disperses (e.g., but not limited to, within 1-60 seconds, 1-45 seconds, 1-30 seconds, 1-15 seconds, etc.), which deteriorates fluoroscopic image quality (FIG. 9), and creates a blurred image. In some embodiments of the present invention, at least one image processing algorithm is utilized to generate a bronchogram. In some embodiments of the present invention, at least one image processing algorithm is utilized to generate an augmented bronchogram.

Figure 14:
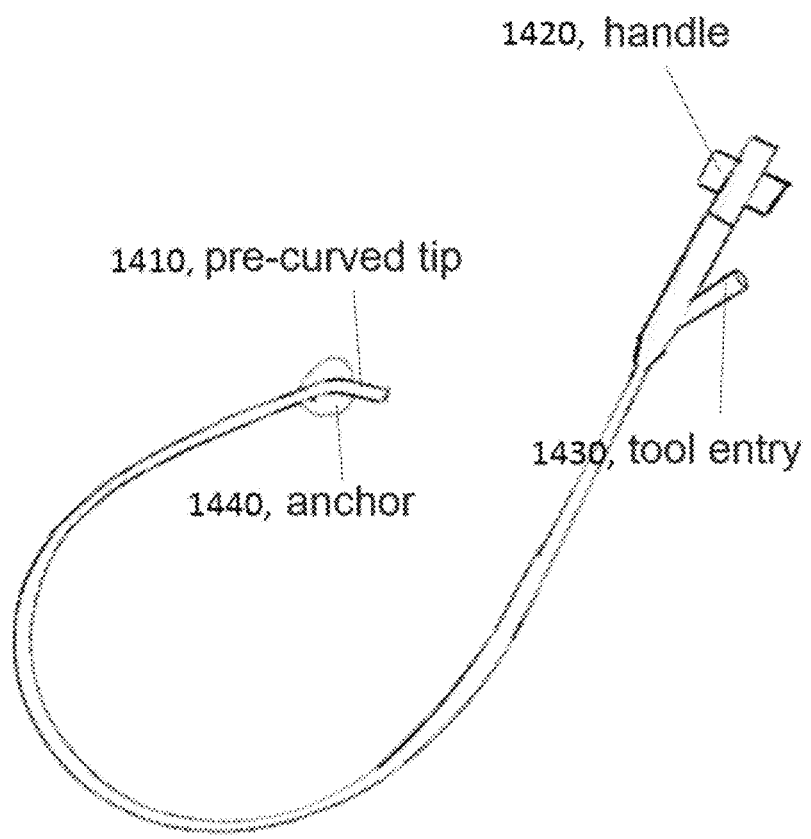
FIG. 14 shows a navigation catheter having an anchor (e.g., disposable or non-disposable catheter) for use in an embodiment of the method of the present invention.

In some embodiments, an augmented bronchogram is created by using at least one radiopaque instrument, that has can optionally have anchoring mechanism as drawn by FIG. 14. In some embodiments, the radioscopic instrument is visible in fluoroscopic images and represents an anatomical structure that can be registered to the bronchial tree, which is identified from at least one preoperative image. In some embodiments, the direct extension of this method is using multiple instrument positions (FIG. 10) extracted and accumulated from temporal fluoroscopic image sequence during the same procedure (FIG. 11). In some embodiments, the radiopaque instrument can be multi-lumen, where lumens can be used for: (i) diagnostic or treatment procedure, (ii) introducing multiple radiopaque guide-wires simultaneously into multiple bronchial airways and using the guide-wires as a plurality of registration references. In some embodiments, this technique improves registration accuracy and robustness.

In some embodiments, an augmented bronchogram is created using at least one instrument that allows perfusion of radiopaque substance to remain visible and in place (e.g., substantially static) for an increased period of time. In some embodiments, the increased period of time is achieved by using the at least one instrument that spreads at least one radiopaque substance on the walls of airways using a brush or sprinkles on the tool exterior. In some embodiments, a radiopaque substance having a high viscosity (e.g., in the form of hydrogel) is injected through the instrument and dispersed on the airways. In some embodiments, the radiopaque material is configured to be gradually released from the radiopaque substance. In some embodiments, the airway area retains a radiopaque characteristic for longer period of time. In some embodiments, a reverse thermo-gelling polymer or similar material is used, to allow effective injection of liquid substance at a low temperature while prevention of fluoroscopic image quality deterioration (FIG. 9) or blurred fluoroscopic image since the injected substance becomes a semisolid gel as the temperature increases to the body temperature.

Figure 13:
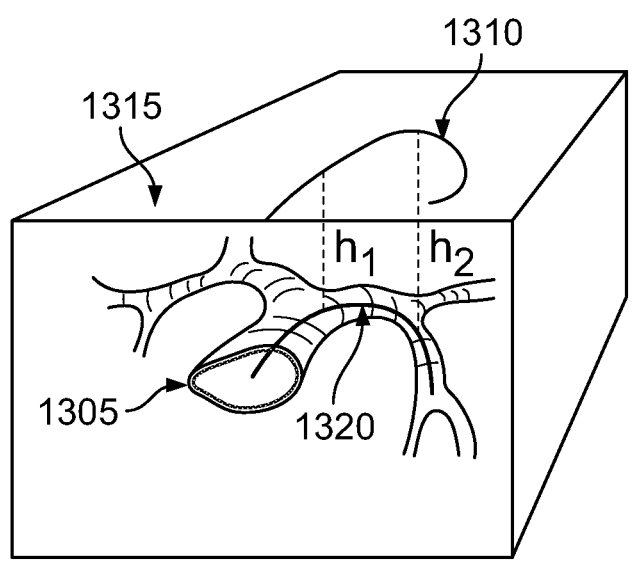
FIG. 13 shows an embodiment of the method of the present invention, illustrating recovery of depth information related to an anatomical path (e.g., a bronchus/i).

In some embodiments, the present invention is a method that includes adding a third dimension (depth) to a position of an instrument on a 2D fluoroscopic image. In some embodiments, a depth of at least one section of the instrument is calculated by (1) comparison of (a) the projected instrument shape on fluoroscopic image with (b) the known anatomical structure of the bronchial airway and (2) making an assumption of constrained instrument location inside the bronchial tree (FIG. 13).

In some embodiments, the present invention is a method that includes adding elevation of the instrument (orientation angle) in a direction perpendicular to a fluoroscopic image. In some embodiments, there are at least two methods to calculate orientation magnitude: (1) comparing the projected and actual physical lengths of a radiopaque straight instrument section, which uses a known zoom (i.e., magnification) of the fluoroscopic image (e.g., from an available registration) (FIG. 12), and (2) using an orientation sensor attached to the instrument to calculate the orientation of the instrument relative to the body of a patient or relative to the fluoroscopic device.

In some embodiments, the method of the present invention includes integrating information including 3D location and orientation to determine the 6 degrees of freedom (DOF) of the instrument inside the patient (e.g., a human body).

In some embodiments, the present invention is a method to track motion and orientation of a tip of an instrument using integrated sensors located on the tip. In some embodiments, the sensor is selected from a group consisting of: a gyroscope, an accelerometer and/or a magnetometer. In some embodiments, the transmitted information from these sensors allows calculating the orientation and the location of the tip in real time. In some embodiments of the present invention, the robustness of the location calculation is improved (i.e., increased accuracy) by assuming/predicting the samples are inside the bronchi. In some embodiments, the samples are registered to the 3D bronchial tree extracted from the preoperative CT image.

In an exemplary embodiment of the present invention, FIG. 7 is a flow chart illustrating method 700. In some embodiments, the flow chart presents the registration process between bronchial airway tree extracted from preoperative image (e.g., but not limited to, a CT scan/image) and airways extracted from fluoroscopic images (e.g., 2, 3, 4, 5, 6, 7, 8, 9, 10, etc.) using an augmented bronchogram. In some embodiments, 710 of the method 700, a CT and/or MRI is a source preoperative and/or intraoperative image. In some embodiments, the preoperative and/or intraoperative image is acquired and transformed into 3D space, and used during surgical treatment and/or diagnostic procedure for a treatment and/or a diagnosis. In an exemplary embodiment, at 720 of the method 700, a 3D bronchial tree is extracted from the image 710 using (1) an automatic segmentation algorithm and/or (2) a manual notation by a physician. In an exemplary embodiment, at 705 of the method 700, there is a source fluoroscopic image and/or fluoroscopic video captured from the fluoroscope. In an exemplary embodiment, at 730 of the method 700, an augmented bronchogram is calculated using fluoroscopic image 705 by one or more approaches disclosed in the present invention.

In some embodiments, the method of the present invention includes an automatic separation/segmentation between soft tissue, bones, instrument(s), an anatomical object(s), and background, where the automatic separation/segmentation uses instrument and/or tissue movement to differentiate between different types of tissues/organs and/or instruments (e.g., movement and/or density) to result in the generation of extracted information (e.g., a bronchial tree).

In an exemplary embodiment, the 3D bronchial tree extracted by 720 and augmented bronchogram extracted by 730, are registered at 740 using the method show in 700. In an exemplary embodiment, the registration process estimates pose information (e.g., position, orientation, and/or camera parameters) of the fluoroscope that would project a 3D bronchial tree to match a 2D augmented bronchogram, and produces a correspondence between 3D space of the image 710 and 2D space of the image 705.

In an embodiment, FIG. 8 shows a sample of augmented bronchogram obtained from a sequence of fluoroscopic images containing an injected radiopaque substance that highlights a partial bronchial tree.

Figure 9:
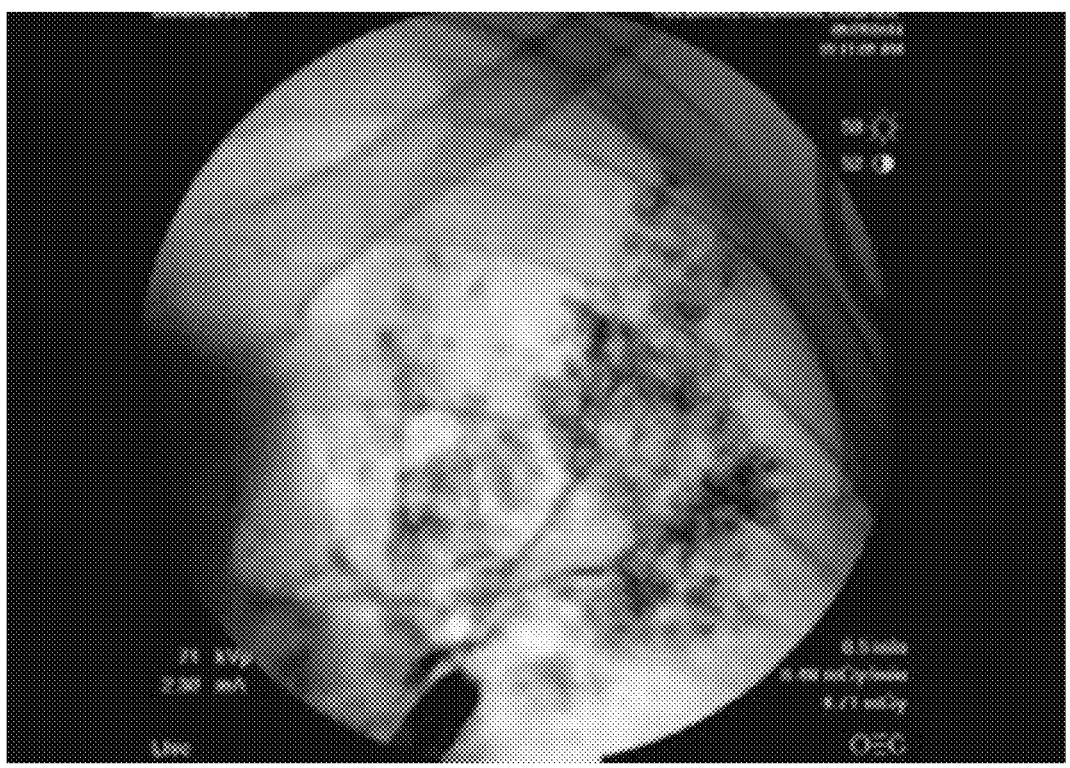
FIG. 9 shows an embodiment of the method of the present invention, illustrating a fluoroscopic image of an area 30 seconds after being injected with a radiopaque substance (e.g., the image appears blurred).

In an embodiment, FIG. 9 shows a fluoroscopic image, which is the same subject as in FIG. 8, but the image was taken after 30 seconds of injection. As shown, the injected radiopaque substance diffuses to the surrounding regions, producing a blurred image. In an embodiment, an augmented bronchogram produces a clear image after 30 seconds of injection.

Figure 10A:
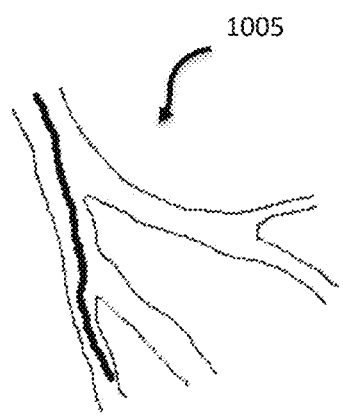
FIGS. 10A, 10B, and 10C show embodiments of the method of the present invention, illustrating navigating through at least one bronchus and/or different bronchi, and recording a fluoroscopic image of each navigating event.
Figure 10B:
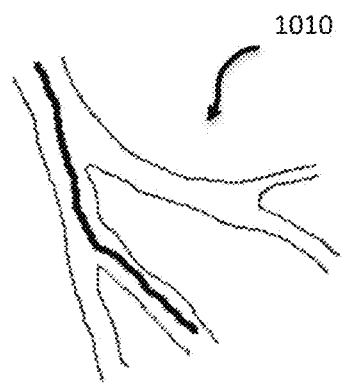
Figure 10C:
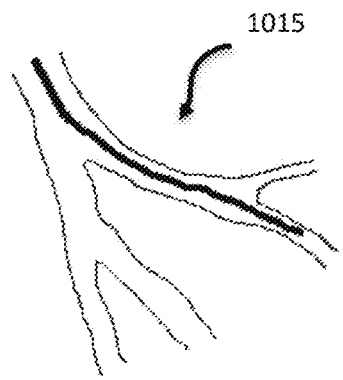
Figure 11:
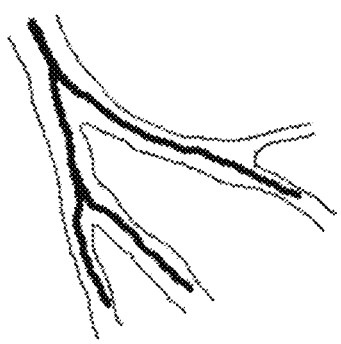
FIG. 11 shows an embodiment of the method of the present invention, illustrating an augmented bronchogram generated/derived from a combination of images (e.g., but not limited to, FIGS. 10A, 10B, and 10C), where the images contain a visible instrument in, e.g., but not limited to, at least one bronchus.

In an embodiment of the present invention, FIG. 10 shows an illustration of the method of use of a radiopaque instrument that is visible on fluoroscopic images. In an embodiment, the images, e.g., 1005, 1010 and 1015, show fluoroscopic views containing a visible instrument in different locations and a schematic structure of a bronchial tree that is not visible in a real fluoroscopic image, and shown here for illustration purposes only. The instrument shown in views 1005, 1010 and 1015 can be the same instrument or different instruments.

In an example, superposition of imaging incorporates distortion correction caused by body movement, breathing, instrument introduction, etc. In some embodiments, the temporal instrument positions are acquired for superposition at the predefined breathing phase.

In an exemplary embodiment, FIG. 11 illustrates the augmented bronchogram, derived from the views 1005, 1010 and 1015 from FIG. 10. In an embodiment, each view adds information regarding the surrounding anatomical structures. In an embodiment, the information is combined to create an augmented bronchogram.

Figure 12:
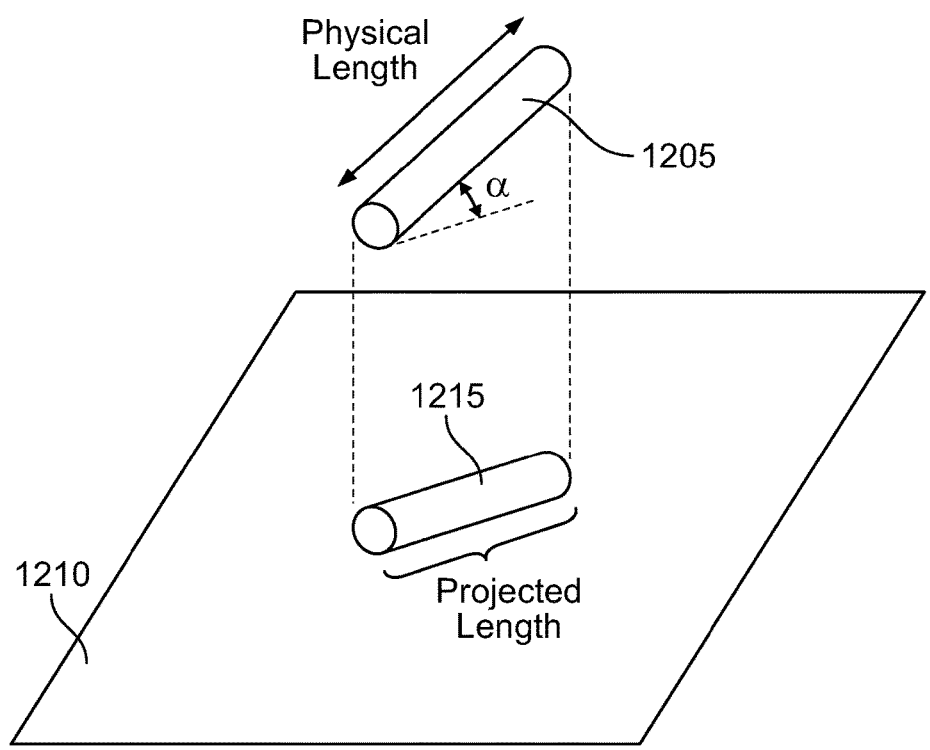
FIG. 12 shows an embodiment of the method of the present invention, illustrating a straight instrument section projected to a fluoroscope image plane.

In an embodiment, FIG. 12 shows a straight section of an instrument 1205, located in the 3D space inside the body. In an embodiment, the instrument is projected on the fluoroscope image plane 1210 and created the projection image 1215. In an embodiment, the angle between the straight section of the instrument 1205 and the fluoroscope image plane 1210 is "alpha."

In an embodiment, FIG. 13 shows a 3D bronchial tree 1315, containing an anatomical path 1320, located inside the airways. In an embodiment, when the 3D anatomical path 1320 is projected on the fluoroscope image plane 1315, the projection 1310 loses the original depth information. In an embodiment, the present invention recovers this information.

In an embodiment, FIG. 14 shows disposable navigation catheter with anchoring, that can be guided by means of pre-curved tip 1410 through the bronchial airways. The tool handle 1420 can be optionally used to enhance navigation performance. The catheter tip can be fixated inside the bronchial airways by means of anchor 1440 that is designed as inflatable balloon or extendable spring, to allow instant multiple access to the area of interest around the catheter tip by medical instrument. The diagnostic and treatment instrument can be introduced through the working channel located inside the navigation catheter at the entry point 1430.

Figures 15A, 15B:
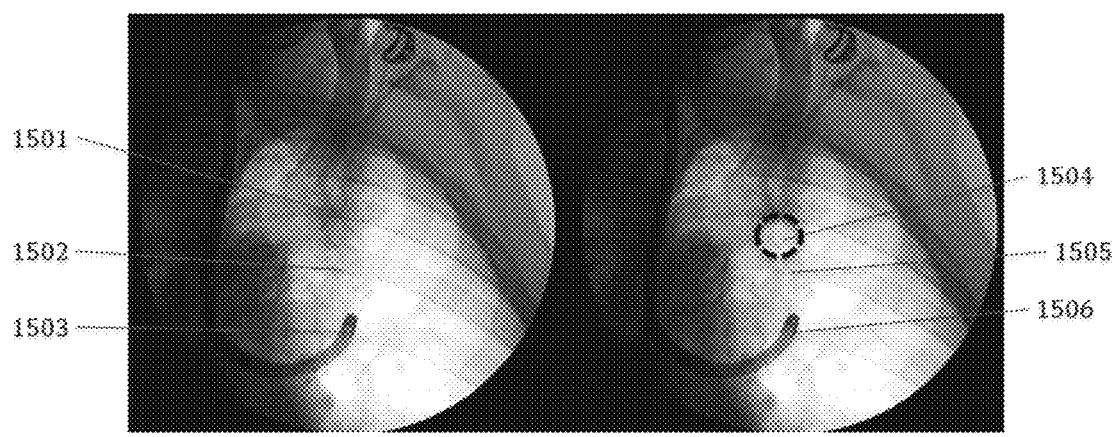
FIGS. 15A and 15B are images showing an embodiment of the results obtained from using the method of the present invention.

In an embodiment, FIG. 15A shows a fluoroscopic image of the diagnostic procedure in human lungs. Biopsy needle 1502 is protruding through working channel of the bronchoscope 1503 to biopsy the suspicious target nodule, which is perceived by physician as dark region 1503. The augmented fluoroscopic image FIG. 15B is generated to highlight the actual nodule area 1504 that was marked by physician prior to procedure on correspondent preoperative CT image of patient chest. The augmented image preserves bronchoscope 1506 and needle 1505 at the original location, however the difference between actual 1506 and perceived 1503 nodule position is obvious. The highlighting technique of 1506 is demonstrated on FIG. 15B, where the yellow color is "injected" into the nodule area of the fluoroscopic image, which is correspondent to one of the CT image (and is further surrounded by a dashed line), while the original information of fluoroscopic image is yet preserved.

In some embodiments, the instant invention is a method and flow that allows using first imaging modality such as CT, MRI, etc., and planning information through generation of augmented image from second imaging modality, such as fluoroscopy, digital subtraction angiography (DSA), etc., with highlighted area of interest or structures and optionally additional imaging and\or planning information, originated from a first imaging modality, superimposed over it comprising: (i) using first imaging modality to obtain at least one first image of chest; (ii) manual or automatic planning of procedure through defining landmarks, area of interest, incision points, critical structures, bifurcations, anatomical organs, etc.; (iii) acquire at least one-second image from second imaging modality, such as fluoroscopy or DSA, and generation of compatible virtual image, such as DRR, from first imaging modality; (iv) mapping of planning data to the objects and structures on the compatible virtual image; (v) registration of at least one second image or video frame from second imaging modality to first image or its portion sourced from first imaging modality; (vi) transfer mapping (i.e., identifying and mapping) of planning data from the compatible virtual image, sourced from first imaging modality to second image from second imaging modality by means of image registration; (vii) highlighting the area of interest, anatomical structures on second image sourced from second imaging modality to obtain third image, wherein the third image is augmented.

In some embodiments, the method further includes superimposing of at least one image or its derivative, it's portion or image based planning information sourced from first imaging modality over second imaging modality. In some embodiments, the method further includes navigation and guidance instructions that aid movement of medical instrument. In some embodiments, the method further includes guidance for positioning second imaging modality, such as fluoroscopic C-Arm, to allow maintaining optimal visibility for the area of interest, incision points, anatomical structures, tool access direction. In some embodiments, the method implements tracking of anatomic structures on subsequent frames from second imaging modality, such as fluoroscopic video, having same acquisition parameters (mode, position, field of view) to allow higher quality of augmented fluoroscopic image through suppression of static anatomic structures and improving signal to noise of underlying soft tissue. In some embodiments, multiphase registration is performed, where the static objects with small movement, such as ribs, are registered at first and more dynamic objects such as diaphragm, bronchi, blood vessels, etc. are gradually registered in the following registration iterations. In some embodiments, the interfering structures being deemphasized. In some embodiments, the compatible virtual image is not generated while the planning data from first imaging modality is transferred to second imaging modality by means of image registration.

In some embodiments, the present invention is a method allowing for the generation of an augmented third image, such as intraoperative fluoroscopic, DSA, etc., with highlighted area of interest or structures comprising: (i) using at least two intraoperative images with known relative movement and rotation to allow grouping pixels of intraoperative image according to their movement variation and intensity values; (ii) performing registration or cross-correlation between at least two sequential intraoperative images to reconstruct structures in the area of interest; (iii) differentiating moving and static structures in the area of interest on user demand; (iv) highlighting anatomical structures on intraoperative image, or any combination thereof. In some embodiments, the method includes using Chest X-ray radiographic image, while the said radiographic image serves as a reference image that enables to enhance anatomical structures on second image through registration or cross-correlation of the information from radiographic image.

In some embodiments, the present invention is an augmented fluoroscopy device that allows generation of augmented fluoroscopy image comprising: a video and image processing unit; a video input card or externally connected device that is capable to input video signal from the variety of Fluoroscopic device; a 3D planning input in internal or DICOM format; an augmented video signal output; or any combination thereof.

In some embodiments, the device is integrated within fluoroscopic device as a module, to obtain RAW data as a signal, and therefore having RAW data input card instead of video input card. In some embodiments, the device is integrated within cone-beam CT system.

In some embodiments, the present invention is a tissue or anatomical structure highlighting technique, where the volume of interest is selected on the image sourcing from first imaging modality, such as CT or MRI; acquired image from second imaging modality; coarse registration is performed between second and first imaging modalities to identify the pose of virtual camera in the second imaging modality correspondent to the one of second imaging modality; at least one pattern is produced from first imaging modality for the anatomical structure around volume of interest; the matching pattern is found in the second imaging modality using single or multiple patterns produced from first imaging modality; the matching pattern from the second imaging modality is enhanced to highlight the anatomy in the volume of interest producing third imaging modality.

In some embodiments of the method of the present invention, when the anatomic structures located outside the area of interest are found and suppressed using the same technique. In some embodiments, the pattern is comprised from anatomical features such as airways, ribs, and blood vessels. In some embodiments, the matching feature from second imaging modality is derived from set of at least one instrument position inside the area of interest.

A method of object depth calculation as follows: given the parameters of compatible virtual image sourcing from first imaging modality, such as DDR—to fluoroscopy; given the pose and field of view of virtual camera, such as virtual fluoroscopic camera, projecting first imaging modality to second imaging modality; determine the object size on virtual image, such as ribs width on DDR at specific location; calculate the depth (such as distance of the specific object or object area from fluoroscopic X-ray source) through comparison between the known object sizes sourced from first image (e.g. CT image) to the one measured on second image (e.g. fluoroscopic image), or any combination thereof. In some embodiments, object size is determined from technical specification instead of or in addition to the measurement on compatible virtual image, such as tool rigid part length or width. In some embodiments, the catheter-type tool is designed to allow the calculation of trajectory as a combination of depth distances from second imaging modality camera center.

A method and flow that allow registration of first three-dimensional imaging modality such as CT, MRI, etc., with second two-dimensional imaging modality of real time x-ray imaging such as fluoroscopy, digital subtraction angiography (DSA), etc. comprising: using first imaging modality to obtain at least one first image of chest; perform manual or automatic segmentation of natural body cavities such as bronchial airways in 3D space; acquire at least one images or sequence of video frames from second imaging modality, such as fluoroscopy or DSA; generation of two-dimensional augmented image generated from second imaging modality that combines unique information to describe the full or partial map of natural body cavities such as portion of bronchial airway tree, abovementioned as augmented bronchogram; calculate registration between first and second imaging modalities through pose estimation by fitting abovementioned corresponded features, or any combination thereof. In some embodiments, an augmented bronchogram is generated using radiopaque material is injected to highlight the body cavity.

In some embodiments, augmented bronchogram is generated through superposition of imaging from at least two different temporal positions of radiopaque instrument located inside the body cavity. In some embodiments, augmented bronchogram is generated through superposition of imaging from at least one different positions of radiopaque instrument located inside the body cavity and angular measurement of C-Arm orientation relative to patient bed. In some embodiments, the radiopaque instrument is designed and configured to reconstruct its three-dimensional space from single projection. In some embodiments, radiopaque substances having a high viscosity such as, but not limited to, hydrogel, reverse thermo-gelling polymer are used to generate augmented bronchogram. In some embodiments, superposition of imaging incorporates distortion correction caused by body movement, breathing, instrument introduction etc. In some embodiments, the temporal instrument positions are acquired for superposition at the predefined breathing phase. In some embodiments, the present invention is a device for navigating inside natural body cavity comprising: guided sheath with anchoring at the tip and guided wire. In some embodiments, the device includes an inflatable balloon serving as anchoring mechanism.

In some embodiments, the instant invention provides a method, including: obtaining a first image from a first imaging modality; identifying on the first image from the first imaging modality at least one element, where the at least one element comprises a landmark, an area of interest, an incision point, a bifurcation, an organ, or any combination thereof, obtaining a second image from a second imaging modality; generating a compatible virtual image from the first image from the first imaging modality; mapping planning data on the compatible virtual image; where mapped planning data corresponds to the at least one element, coarse registering of the second image from the second imaging modality to the first image from the first imaging modality; identifying at least one element of the mapped planning data from the compatible virtual image; identifying at least one corresponding element on the second imaging modality; mapping the at least one corresponding element on the second imaging modality; fine registering of the second image from the second imaging modality to the first image from the first imaging modality; generating a third image; where the third image is an augmented image including a highlighted area of interest.

In some embodiments, the method further includes superimposing the at least one image, a portion of the at least one image, or a planning information derived from the first imaging modality over the second imaging modality. In some embodiments, the method further includes using at least one instruction, where the at least one instruction can include information regarding navigation, guidance, or a combination thereof. In some embodiments, the guidance includes information regarding a positioning of a device shown the second imaging modality, where the device comprises a fluoroscopic C-Arm, as to result in achieving visibility for the area of interest, incision points, anatomical structures, or tool access direction. In some embodiments, the method further includes tracking of at least one anatomical structure by use of at least one subsequent image derived from the second imaging modality, where the second imaging modality comprises a fluoroscopic video configured to have substantially the same acquisition parameters, and where the acquisition parameters comprise mode, position, field of view, or any combination thereof, to generate the augmented fluoroscopic image by suppressing static anatomic structures and/or improving signal to noise of underlying soft tissue. In some embodiments, the method further includes performing a multiphase registration, where the at least one substantially static object is first registered; and where at least one dynamic object is second registered, where the at least one dynamic object comprises a diaphragm, a bronchus, a blood vessel, or any combination thereof. In some embodiments, the method further includes deemphasizing at least one interfering structure. In some embodiments, the compatible virtual image is not generated while the planning data from first imaging modality is transferred to second imaging modality by means of image registration.

In some embodiments, the instant invention provides a method, including:

using at least two intraoperative images with known relative movement and rotation to generate a grouping of pixels derived from an intraoperative image, where the grouping of pixels is determined by individual calculation of each pixel using: (a) movement variation of each pixel and (b) intensity values of each pixel; performing registration using at least two sequential intraoperative images to reconstruct structures in an area of interest; differentiating moving structures from static structures in the area of interest; and highlighting anatomical structures on at least one intraoperative image. In some embodiments, the method further includes using a chest x-ray radiographic image as a first intraoperative image.

In some embodiments, the instant invention provides a system including an augmented fluoroscopy device configured to generate an augmented fluoroscopy image including (a) video and image processing unit, (b) video input card or externally connected device configured to input video signal a fluoroscopic device, (c) 3D planning input in internal or DICOM format, (d) an augmented video signal output, or any combination thereof. In some embodiments, the system is integrated with at least one fluoroscopic device is a module including a RAW data input card (i.e., instead of a video input card) configured to obtain RAW data as a signal. In some embodiments, the system is integrated with a Cone-beam CT system.

In some embodiments, the instant invention provides a system including an instrument for navigating inside natural body cavity including: (a) a guided sheath with anchoring at the tip and/or (b) a guided wire. In some embodiments, the instrument is an inflatable balloon configured to act as an anchoring mechanism.

In some embodiments, the instant invention provides a method including: (i) selecting a volume of interest on a first image from a first imaging modality; (ii) generating a second image from a second imaging modality; (iii) coarse registering using the first imaging modality and the second imaging modality; (iv) producing at least one pattern from the first imaging modality; (v) generating a matching pattern by use of the second imaging modality using single or multiple patterns produced from first imaging modality; (vi) enhancing the matching pattern from the second imaging modality to highlight the anatomy in the volume of interest for producing third imaging modality. In some embodiments, the anatomic structures located outside the area of interest are found and suppressed using substantially the same method. In some embodiments, the pattern includes anatomical features including, but not limited to, airways, ribs, and blood vessels. In some embodiments, the matching feature from second imaging modality is derived from a set of at least one instrument position inside the area of interest.

In some embodiments, the instant invention provides a method including: using a first imaging modality to obtain at least one first image of a patient's chest; segmenting natural body cavities including bronchial airways in a 3D space; generating at least one image from a second imaging modality; generating a two-dimensional augmented image generated from the second imaging modality by combining information, where the information describes a complete map or a partial map of natural body cavities, including a bronchial airway tree; calculating registration between the first imaging modality and the second imaging modality as pose estimation between the portion of bronchial airway sourcing from second imaging modality and segmented map of bronchial airway sourcing from first imaging modality; calculating registration between first and second imaging modalities through pose estimation by mapping corresponding features. In some embodiments, the augmented bronchogram is generated using radiopaque material is injected to highlight the body cavity. In some embodiments, the augmented bronchogram is generated through superposition of imaging from at least three two different positions of radiopaque instrument located inside the body cavities. In some embodiments, an augmented bronchogram is generated through superposition of imaging from at least one different positions of radiopaque instrument located inside the body cavity and angular measurement of C-Arm orientation relative to patient bed. In some embodiments, the radiopaque instrument is designed and configured to reconstruct its three-dimensional space from single projection. In some embodiments, the radiopaque substance(s) having a high viscosity such as, but not limited to, hydrogel, reverse thermo-gelling polymer can be used to generate augmented bronchogram.

In some embodiments, the instant invention provides a method including: providing the parameters of compatable virtual image sourcing from first imaging modality, such as, but not limited to, DDR—to fluoroscopy; determining an object size on virtual image, such as, but not limited to, ribs width on DDR at specific location; providing the pose and field of view of a virtual camera, such as, but not limited to, a virtual fluoroscopic camera, projecting first imaging modality to second imaging modality such as fluoroscopic camera calculated from calibration process; determining the object size on the virtual image, such as ribs width on DDR at specific location; calculating the depth (for example, but not limited to, distance of the specific object or object area from fluoroscopic X-ray source) through comparison between the known object sizes sourced from first image (e.g. CT image) to the one measured on second image (e.g. fluoroscopic image). In some embodiments, the object size is determined from technical specification instead of or in addition to the measurement on compatible virtual image, such as tool rigid part length or width. In some embodiments, the catheter-type tool is designed to allow the calculation of trajectory as a combination of depth distances from second imaging modality camera center.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method, comprising:
    obtaining a first image from a first imaging modality;
    identifying on the first image from the first imaging modality at least one element, wherein the at least one element comprises a landmark, an area of interest, an incision point, a bifurcation, an organ, or any combination thereof;
    obtaining a second image from a second imaging modality;
    generating an augmented bronchogram image from the second imaging modality, wherein the augmented bronchogram image is generated by:
        placing a radiopaque instrument inside a body cavity at a first position, generating a first image of the radiopaque instrument inside the body cavity at the first position,
        placing the radiopaque instrument inside the body cavity at a second position, generating a second image of the radiopaque instrument inside the body cavity at the second position,
        superpositioning the first image of the radiopaque instrument inside the body cavity at the first position with the second image of the radiopaque instrument inside the body cavity at the second position to generate the augmented bronchogram;
    wherein the first position and the second position are different;
    wherein the augmented bronchogram is a map of a bronchial airway tree;
    generating a compatible virtual image from the first image from the first imaging modality;
    coarse registering of the augmented bronchogram from the second imaging modality to the compatible virtual image from the first imaging modality;
    fine registering of the augmented bronchogram image from the second imaging modality to the compatible virtual image from the first imaging modality;
    generating a third image; wherein the third image is an augmented image including a highlighted area of interest,
    wherein the highlighted area of interest can be determined by a method selected from the group consisting of:
        (i) bolding a portion of the augmented bronchogram image,
        (ii) coloring the portion of the augmented bronchogram image,
        (iii) enhancing the portion of the augmented bronchogram image,
        (iv) super-positioning a graphic over the augmented bronchogram image,
        (v) or any combination thereof.

2. The method of claim 1, further comprising superimposing the first image, a portion of the first image, or a first planning data derived from the first imaging modality over the second image of the second imaging modality.

3. The method of claim 1, further comprising using at least one instruction, wherein the at least one instruction can include information regarding navigation, guidance, or a combination thereof.

4. The method of claim 3, wherein the guidance includes information regarding the first position of the radiopaque instrument shown by the second imaging modality, wherein the radiopaque instrument comprises a fluoroscopic C-Arm, to result in achieving visibility for the area of interest, incision points, anatomical structures, or tool access direction.

5. The method of claim 1, further comprising tracking of at least one anatomical structure by use of at least one subsequent image derived from the second imaging modality,
wherein the second imaging modality comprises a fluoroscopic video configured to have substantially the same acquisition parameters, and
wherein the acquisition parameters comprise mode, position, field of view, or any combination thereof, to generate the augmented fluoroscopic image by suppressing static anatomic structures, improving signal to noise of underlying soft tissue, or any combination thereof.

6. The method of claim 1, further comprising performing a multiphase registration,
wherein the at least one substantially static object is first registered; and
wherein at least one dynamic object is second registered,
wherein the at least one dynamic object comprises a diaphragm, a bronchus, a blood vessel, or any combination thereof.

7. The method of claim 1, further comprising deemphasizing at least one interfering structure.

8. The method of claim 2, wherein the compatible virtual image is not generated while the planning data from first imaging modality is transferred to second imaging modality by means of image registration.

9. The method of claim 1, wherein the augmented bronchogram is a partial map of the bronchial airway tree.

10. The method of claim 1, wherein the augmented bronchogram is a complete map of the bronchial airway tree.

11. The method of claim 1, wherein the augmented bronchrogram image is further generated by a method selected from the group consisting of:
a) superpositioning the first position of the radiopaque instrument, the second position of the radiopaque instrument in the body cavity, and their correspondent angular measurement of a C-arm orientation relative to the patient, or any combination thereof;
b) using a radiopaque instrument configured to reconstruct a three-dimensional space from a single projection;
b) or any combination thereof.

\* \* \* \* \*